(12) United States Patent
Landon et al.

(10) Patent No.: US 11,098,114 B2
(45) Date of Patent: Aug. 24, 2021

(54) OVINE DERIVED HUMAN TNFα POLYCLONAL ANTIBODY COMPOSITION FOR ORAL ADMINISTRATION

(71) Applicant: MICROPHARM LIMITED, Newcastle Emlyn (GB)

(72) Inventors: John Landon, Newcastle Emlyn (GB); Ruth Elizabeth Coxon, Newcastle Emlyn (GB)

(73) Assignee: MICROPHARM LIMITED, Newcastle Emlyn (GB)

( * ) Notice: Subject to any disclaimer, the term of this patent is extended or adjusted under 35 U.S.C. 154(b) by 0 days.

(21) Appl. No.: 16/481,439

(22) PCT Filed: Jan. 29, 2018

(86) PCT No.: PCT/GB2018/050244
§ 371 (c)(1),
(2) Date: Jul. 26, 2019

(87) PCT Pub. No.: WO2018/138524
PCT Pub. Date: Aug. 2, 2018

(65) Prior Publication Data
US 2019/0338021 A1 Nov. 7, 2019

(30) Foreign Application Priority Data
Jan. 27, 2017 (GB) .................... 1701404

(51) Int. Cl.
*C07K 16/24* (2006.01)
*A61P 1/04* (2006.01)
*A61K 9/00* (2006.01)
*A61K 47/42* (2017.01)
*A61K 47/46* (2006.01)

(52) U.S. Cl.
CPC .......... *C07K 16/241* (2013.01); *A61K 9/0053* (2013.01); *A61K 47/42* (2013.01); *A61K 47/46* (2013.01); *A61P 1/04* (2018.01)

(58) Field of Classification Search
None
See application file for complete search history.

(56) References Cited

U.S. PATENT DOCUMENTS 8,921,529 B2 * 12/2014 Shone ................ C07K 16/1282
530/389.5
2013/0011415 A1  1/2013  van Neerven et al.
2013/0337018 A1  12/2013  Fox

FOREIGN PATENT DOCUMENTS

| JP | H08511015 A | 11/2019 |
| WO | WO1994029347 | 12/1994 |
| WO | WO199964069 A1 | 12/1999 |
| WO | WO2001030373 A1 | 5/2001 |
| WO | WO2008127105 A1 | 10/2008 |
| WO | WO2009046168 A1 | 4/2009 |
| WO | WO2011047328 A1 | 4/2011 |
| WO | WO2011067616 A1 | 6/2011 |
| WO | WO2013019889 A2 | 2/2013 |
| WO | WO2014165226 A2 | 10/2014 |
| WO | WO2018138524 A1 | 8/2018 |

OTHER PUBLICATIONS

Yadav et al., Gastrointestinal stability of therapeutic anti-TNFα IgG1 monoclonal antibodies, Int. J. Pharmaceutics 502, 181-187, 2016. (Year: 2016).*
Birk Y. The Bowman—Birk inhibitor, Int. J. Peptide Res., 25, 113-131, 1985. (Year: 1985).*
Bhol, et al., "AVX-470: a novel oral anti-TNF antibody with therapeutic potential in inflammatory bowel disease," Inflamm. Bowel Dis., vol. 19, No. 11, 2013, pp. 2273-2281.
Search Report dated Nov. 7, 2017 in Great Britain Application No. 1701404.4, 7 pages.
Search Report and Written Opinion dated Mar. 20, 2018 in International Application No. PCT/GB2018/050244, 14 pages.
Hedegaard & Heegaard, "Passive immunisation, an old idea revisited: Basic principles and application to modern animal production systems," Vet. Immunol. Immunopathol., vol. 174, 2016, pp. 50-63.
Jasion, et al., "Survival and digestibility of orally-administered immunoglobulin preparations containing IgG through the gastrointestinal tract in humans," Nutrition Journal, vol. 14, 2015, 8 pages.
Newcombe, et al., "Antibody production: polyclonal-derived biotherapeutics," Journal of Chromatography B., vol. 848, No. 1, 2007, pp. 2-7.
Office Action dated Jul. 28, 2020 in European Application No. 18702801.4, 6 pages.
Qiu, et al., "The evolving experience with therapeutic TNF inhibition in sepsis: considering the potential influence of risk of death," Expert Opin. Investig. Drugs, vol. 20, No. 11, 2011, pp. 1555-1564.
Ehehalt and Krammer, "Current diagnostics and therapy of ulcerative colitis," Coloproctology, vol. 36, 2014, pp. 409-420.
Fox, et al., "TNF and Oral Mucositis: Repsonse to effect of selective inhibitors of inflammation on oral musocitis: Preclinical Studies," Radiother. Oncol., vol. 92, 2009, 1 page.
Gardiner, et al., "Effect of sheep antibodies to human TNF-alpha and IL-1beta on cardiovascular responses to lipopolysaccharide (LPS) in conscious rats," Brit. J. Pharmacal., vol. 123, 1998, 1 page.
Search Report dated Jan. 9, 2019 for Great Britain Application No. 1812261.4, 4 pages.
Search Report dated Jan. 10, 2019 for Great Britain Application No. 1812262.2, 4 pages.
Jones and Martino, "Targeted localized use of therapeutic antibodies: a review of non-systemic, topical and oral applications," Cri. Rev. Biotechnol., vol. 2015, 2015, 15 pages.

(Continued)

*Primary Examiner* — Elly-Gerald Stoica
(74) *Attorney, Agent, or Firm* — Lee & Hayes PC; C. Rachal Winger; Thu Nguyen

(57) ABSTRACT

The present invention is directed to an antibody composition for oral administration comprising intact blood-derived polyclonal antibodies that bind to a human tumour necrosis factor α (TNFα), and means for protecting the antibodies during gastrointestinal transit, as well as methods for manufacturing, kits, and therapeutic uses of the same.

13 Claims, 2 Drawing Sheets

Specification includes a Sequence Listing.

(56) References Cited

OTHER PUBLICATIONS

Office Action dated Aug. 28, 2020 in Japanese Application No. 2019-533211, 10 pages.
Kumar, et al., "Golimumab in ulcerative colitis: A multi-centre real-world experience," J. Crohn's Colitis, vol. 12, Suppl. 1, 2018, 2 pages.
Porter, et al., "Pharmacokinetics of ovine derived polyclonal anti-TNFalpha antibody Cytotab (tm) in sepsis," Clin. Pharmacol. Thera., vol. 59, No. 2, 1996, 1 page.
Rojas, et al., "Caprylic acid fractionation of hyperimmune horse plasma: Description of a simple procedure for antivenom production," Toxicon, vol. 32, No. 3, 1994, pp. 351-363.
Russo, et al., "Purification of IgG monoclonal antibody by caprylic acid precipitation," J. Immunol. Meth., vol. 65, 1983, pp. 269-271.
Search Report and Written Opinion dated Oct. 9, 2019 in International Application No. PCT/GB2019/052120, 15 pages.
Search Report and Written Opinion dated Oct. 9, 2019 for International Application No. PCT/GB2019/052121, 14 pages.
Symon, et al., "A murine model for the study of molecular pathogenesis of radiation proctitis," Int. J. Radiation, Oncol. Bio. Phys., vol. 76, 2010, pp. 242-250.
Van der Hagen, et al., "Anti-tnf-alpha (Infliximab) used as induction treatment in case of active proctitis in a multistep strategy followed by definitive surgery of complex anal fistulas in Crohn's disease:A preliminary report," Dis. Colon Rectum, vol. 48, 2005, pp. 758-767.
Herbertson, et al., "Anti-tumor Necrosis Factor-alpha Prevents Decreased Ventricular Contractility in Endotoxemic Pigs," Am. J. Respir. Crit. Care Med., vol. 152, No. 2, 1995, pp. 480-488.
Office Action dated Mar. 30, 2021 in Japanese Application No. 2019-533211, 7 pages.

\* cited by examiner

SEQUENCE LISTING

<160> NUMBER OF SEQ ID NOS: 13

<210> SEQ ID NO 1
<211> LENGTH: 157
<212> TYPE: PRT
<213> ORGANISM: Homo sapiens

<400> SEQUENCE: 1

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 2
<211> LENGTH: 233
<212> TYPE: PRT
<213> ORGANISM: Homo sapiens

<400> SEQUENCE: 2

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                      55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230
```

<210> SEQ ID NO 3
<211> LENGTH: 146
<212> TYPE: PRT
<213> ORGANISM: Homo sapiens

<400> SEQUENCE: 3

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                      55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125
```

```
Glu Gly Leu Tyr Leu Ile Tyr Ser Gln Val Leu Phe Lys Gly Gln Gly
    130                 135                 140

Cys Pro
145

<210> SEQ ID NO 4
<211> LENGTH: 70
<212> TYPE: PRT
<213> ORGANISM: Homo sapiens

<400> SEQUENCE: 4

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro
65                  70

<210> SEQ ID NO 5
<211> LENGTH: 8
<212> TYPE: PRT
<213> ORGANISM: Homo sapiens

<400> SEQUENCE: 5

Val Arg Ser Ser Ser Arg Thr Pro
1               5

<210> SEQ ID NO 6
<211> LENGTH: 18
<212> TYPE: PRT
<213> ORGANISM: Homo sapiens

<400> SEQUENCE: 6

His Val Val Ala Asn Pro Gln Ala Glu Gly Gln Leu Gln Trp Leu Asn
1               5                   10                  15

Arg Arg

<210> SEQ ID NO 7
<211> LENGTH: 6
<212> TYPE: PRT
<213> ORGANISM: Homo sapiens

<400> SEQUENCE: 7

Asn Gly Val Glu Leu Arg
1               5

<210> SEQ ID NO 8
<211> LENGTH: 5
<212> TYPE: PRT
<213> ORGANISM: Homo sapiens

<400> SEQUENCE: 8

Val Pro Ser Glu Gly
1               5
```

```
<210> SEQ ID NO 9
<211> LENGTH: 7
<212> TYPE: PRT
<213> ORGANISM: Homo sapiens

<400> SEQUENCE: 9

Cys Pro Ser Thr His Val Leu
1               5

<210> SEQ ID NO 10
<211> LENGTH: 11
<212> TYPE: PRT
<213> ORGANISM: Homo sapiens

<400> SEQUENCE: 10

Ile Ser Arg Ile Ala Val Ser Tyr Gln Thr Lys
1               5                   10

<210> SEQ ID NO 11
<211> LENGTH: 13
<212> TYPE: PRT
<213> ORGANISM: Homo sapiens

<400> SEQUENCE: 11

Pro Cys Gln Arg Glu Thr Pro Glu Gly Ala Glu Ala Lys
1               5                   10

<210> SEQ ID NO 12
<211> LENGTH: 16
<212> TYPE: PRT
<213> ORGANISM: Homo sapiens

<400> SEQUENCE: 12

Asp Arg Leu Ser Ala Glu Ile Asn Arg Pro Asp Tyr Leu Asp Phe Ala
1               5                   10                  15

<210> SEQ ID NO 13
<211> LENGTH: 233
<212> TYPE: PRT
<213> ORGANISM: Homo sapiens

<400> SEQUENCE: 13

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Leu Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
        130                 135                 140
```

-continued

```
Cys Pro Ser Thr His Val Leu Leu Thr His Thr Ile Ser Arg Ile Ala
145             150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225             230
```

OVINE DERIVED HUMAN TNFα POLYCLONAL ANTIBODY COMPOSITION FOR ORAL ADMINISTRATION

CROSS-REFERENCE TO RELATED APPLICATIONS

This application is a U.S. National Phase Patent Application based on PCT/GB2018/050244, filed on Jan. 29, 2018, which claims priority to Great Britain Patent Application No. 1701404.4, filed on Jan. 27, 2017, the entire contents of each of which is incorporated by reference herein.

REFERENCE TO SEQUENCE LISTING

The Sequence Listing associated with this application is provided in text format in lieu of a paper copy, and is hereby incorporated by reference into the specification. The name of the text file containing the Sequence Listing is 2416589 ST25.txt. The text file is 8.86 KB, was created on Jun. 10, 2019, and is being submitted electronically via EFS-Web.

The present invention relates to an antibody therapeutic suitable for use in treating inflammatory disorders.

Tumour necrosis factor α (TNFα) is a principal cytokine mediating systemic inflammation, and is implicated in a number of diseases and disorders including septic shock, as well as gastrointestinal disorders, such as inflammatory bowel disease.

The two main forms of chronic inflammatory bowel disease (IBD) are ulcerative colitis (UC) and Crohn's disease (CD). UC and CD affect more than five million people in Europe and North America and their incidence is increasing globally. Both are the result of dysregulation of intestinal immune homeostasis characterised by markedly elevated levels of both soluble and membrane-bound TNFα in the intestinal wall. Due to the chronic nature of these diseases long-term therapy is a requirement. With this in mind current antibody therapeutics rely on systemic administration of monoclonal antibodies directed against TNFα. Such monoclonal antibodies are typically chimeric or humanised with a view to avoiding induction of a humoral immune response in the patient. The use of polyclonal antibodies of animal origin has been avoided due to the risk of triggering such a response. Three monoclonal antibodies currently in widespread use are the chimeric murine Infliximab, and fully humanised Adalimumab and Etanercept. Infliximab is infused intravenously while the other two are infused intravenously.

Systemic use of antibodies has been associated with infusion reactions and such treatment is inconvenient for out-patients since intravenous infusions usually require a short stay in hospital. Additionally, the efficiency with which a systemically administered McAb (Molecular Weight ~150, 000 Da) will pass from the blood to the tissue fluid and then cross the layers of the gastrointestinal tract to reach the inflamed lining of the epithelium is also questionable. Moreover, since TNFα is a cytokine that plays an important pro-inflammatory role systemically in protecting patients from infection, long-term systemic administration of anti-TNFα antibodies is associated with an increased incidence of serious side-effects including reactivation of tuberculosis, opportunistic infections, demyelinating diseases and a long term risk of lymphoma.

The present invention solves at least one of the above-mentioned problems.

The present inventors have surprisingly found that intact blood-derived antibodies that bind TNFα, when suitably formulated for oral administration, constitute an improved therapeutic for inflammatory disorders, such as IBD.

Polyclonal TNFα antibodies derived from blood, and formulated in a composition of the present invention when given orally surprisingly exhibit improved efficacy and exhibit improved specific titres when compared to conventionally manufactured antibodies (e.g. milk-derived antibodies).

In particular, polyclonal TNFα antibodies manufactured in an ovine or equine host (preferably ovine host), and formulated in a composition of the present invention when given orally, surprisingly exhibit improved efficacy and improved specific titres when compared to conventionally manufactured antibodies.

Additionally, or alternatively polyclonal antibodies of the invention when administered orally to a subject elicit no, or greatly-reduced, side-effects (e.g. humoral immune response side-effects) when compared to conventional antibodies (e.g. monoclonal antibodies) given systemically. Hence, the composition of the invention is suitable for prolonged therapeutic use, unlike systemically administered antibody compositions.

As a further advantage, manufacture of said polyclonal antibodies is much less expensive than conventional monoclonal antibodies. Hence, the present invention provides a scalable and/or cost-efficient therapeutic.

In one aspect the invention provides an antibody composition for oral administration comprising intact blood-derived polyclonal antibodies that bind a human tumour necrosis factor α (TNFα), and means for protecting the antibodies during gastrointestinal transit.

Advantageously, blood-derived polyclonal antibodies to TNFα can be obtained multiple times from the blood of the same host without killing said host. This is in contrast to conventional methods using sources such as bovine colostrum, which only yields antibodies for a limited time (e.g. once).

The blood-derived antibodies may be obtainable from a non-human mammal.

The term "obtainable" as used herein also encompasses the term "obtained". In one embodiment the term "obtainable" means obtained.

Preferably the antibodies are ovine or equine polyclonal antibodies.

More preferably, the antibodies are ovine polyclonal antibodies (e.g. obtainable from an ovine).

Thus, in one aspect there is provided an antibody composition for oral administration comprising intact ovine polyclonal antibodies that bind to a human tumour necrosis factor α (TNFα), and means for protecting the antibodies during gastrointestinal transit.

An antibody of the present invention binds to and neutralises human tumour necrosis factor α (TNFα). The antibody binds to human TNFα with a higher binding affinity than for a non-human TNFα or an alternative antigen. In one embodiment an antibody of the invention binds to human TNFα with an affinity (measured by the dissociation constant: $K_d$) of at least $10^{-4}$ M or at least $10^{-5}$ M. In one embodiment an antibody of the invention may bind to human TNFα with an affinity ($K_d$) of at least $10^{-6}$ M or $10^{-7}$ M. Suitably an antibody of the invention may bind to human TNFα with an affinity ($K_d$) of at least $10^{-8}$ M or $10^{-9}$ M.

Alternatively or additionally, antibody binding affinity may be measured by way of the association constant ($K_a$). In one embodiment an antibody of the invention binds to human TNFα with an affinity (measured by the association constant: $K_a$) of at least $10^6$ M. Suitably an antibody of the invention binds to human TNFα with an affinity (measured by the association constant: $K_a$) of at least at least $10^7$M (e.g. at least $10^8$ M).

Antibody binding can be tested using the assay described in Example 3. Neutralisation can be tested using the assay described in Example 4. In more detail, an antibody composition can be assayed to test neutralisation of the cytotoxic effect of TNFα on a L929 mouse fibrosarcoma cell line.

Surprisingly, blood-derived antibodies obtainable from a non-human mammal (preferably an ovine and/or an equine non-human mammal) immunised with human TNFα (or a purified fraction thereof) contains a much higher concentration of antibodies specific for human TNFα, when compared to other non-blood-derived sources (e.g. avian [for example from egg yolk] or bovine sources, such as milk). In some cases the concentration of specific antibodies in said blood (e.g. serum or plasma) or purified fraction thereof is 100 times greater.

In one embodiment at least 5% (suitably at least 10%) of the total antibodies comprised in a blood sample obtainable from a host (e.g. non-human mammal) immunised with human TNFα (or a purified fraction thereof) binds to human TNFα. In another embodiment at least 15% or 20% (suitably at least 25% or at least 30%) of the total antibodies comprised in a blood sample obtainable from a hots (e.g. non-human mammal) immunised with human TNFα (or a purified fraction thereof) binds to human TNFα.

In one embodiment at least 5% (suitably at least 10%) of the total antibodies comprised in antisera obtainable from an ovine immunised with human TNFα (or a purified fraction thereof) binds to human TNFα. In another embodiment at least 15% or 20% (suitably at least 25% or at least 30%) of the total antibodies comprised in antisera obtainable from an ovine immunised with human TNFα (or a purified fraction thereof) binds to human TNFα.

In one embodiment at least 5% (suitably at least 10%) of the total antibodies comprised in blood plasma obtainable from an equine immunised with human TNFα (or a purified fraction thereof) binds to human TNFα. In another embodiment at least 15% or 20% (suitably at least 25% or at least 30%) of the total antibodies comprised in blood plasma obtainable from an equine immunised with human TNFα (or a purified fraction thereof) binds to human TNFα.

In one embodiment an antibody composition comprises intact polyclonal antibodies at a concentration of 5-100 g/L or 10-75 g/L. In one embodiment an antibody composition comprises intact polyclonal antibodies at a concentration of 20-75 g/L or 35-60 g/L. Suitably, an antibody composition may comprise at least about 20 or 50 g/L of intact polyclonal antibodies. The concentrations referred to may be the concentrations of total intact polyclonal antibodies, suitably total intact polyclonal IgG (i.e. including antibodies that do, as well as do not, bind to TNFα). In one embodiment the foregoing embodiments refer to intact polyclonal antibodies that bind to TNFα. Preferably the antibodies referred to are ovine polyclonal antibodies.

An "antibody" is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference). Preferably, each VHC and VLC is composed of three CDRs and four FRs, arranged from amino-terminus to carboxy-terminus in the following order: FR1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulphide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda. Preferably an antibody of the invention is an intact IgG.

The term "intact antibody" is used herein to distinguish an antibody of the invention from an antibody fragment (e.g. an antibody Fab, F(ab)$_2$ or Fc). An "intact antibody" therefore comprises (or consists of) each of the antibody regions/domains present in a full-length antibody (e.g. obtainable from an ovine). A monomer of an "intact antibody" comprises (or consists of) two heavy chains, and two light chains. The heavy chains each comprise (or consist of) a VH domain, a CH1 domain, a CH2 domain, and a CH3 domain. The light chains each comprise (or consist of) a CL domain and a VL domain.

Thus, an antibody composition of the present invention comprises no or substantially no antibody fragments (e.g. Fab, F(ab)$_2$ or Fc fragments). The term "substantially no" as used in this context means that less than 5%, 4%, 3%, 2%, 1%, 0.5%, 0.1%, or 0.01% of the total concentration of antibodies comprised in a composition of the invention are antibody fragments. Conversely in one embodiment at least 95%, 96%, 97%, 98%, 99%, 99.5%, 99.9%, 99.99% or 100% (suitably 100%) of the total concentration of antibodies comprised in the composition are intact antibodies. In one embodiment a polyclonal antibody may be purified and/or isolated from contaminating antibody fragments.

Advantageously, the intact antibodies of the invention demonstrate improved TNFα binding and/or neutralisation when compared to antibody fragments, as demonstrated by an improved TNFα binding capability (Example 3) and/or neutralisation capability (Example 4). Moreover, the intact antibodies of the invention are much less expensive to produce than antibody fragments which require additional processing and/or purification steps.

In one aspect the invention provides a method for manufacturing intact blood-derived polyclonal antibodies that bind to human tumour necrosis factor α (TNFα), said method comprising obtaining a blood sample from a non-human mammal that has been administered an immunogen comprising human TNFα or a fragment thereof. The blood sample comprises intact polyclonal antibodies that bind to human TNFα. The invention also relates to antibodies obtainable by said method.

The blood sample may be further processed, e.g. to obtain serum or blood plasma. The antibody may therefore be obtainable from blood serum or blood plasma. In embodiments where the non-human mammal is an ovine the antibodies may be obtainable from blood serum. In embodiments where the non-human mammal is an equine the antibodies may be obtainable from blood plasma.

The term "blood-derived" as used herein means that the antibodies are obtained from the blood of a host (e.g. non-human mammal) used to produce said antibodies. Typically blood-derived antibodies may be obtained by administering human TNFα or a fragment thereof to said host (e.g. non-human mammal) subcutaneously, intramuscularly, intraperitoneally, and/or intravenously.

In one embodiment a blood sample (e.g. serum) comprises at least 1, 2, 3, 4, 5, 6, 7, or 8 g/L of antibodies that bind to human TNFα, preferably at least 3 or at least 5 g/L of antibodies that bind to human TNFα.

In one embodiment a blood sample (e.g. serum) comprises about 1 to about 12 g/L of antibodies that bind to human TNFα, for example about 3 to about 9 g/L of antibodies that bind to human TNFα.

The method may further comprise admixing blood-derived polyclonal antibodies with means for protecting said antibodies during gastrointestinal transit.

In one embodiment a blood sample comprises antibodies that bind to human TNFα with an avidity of at least $1 \times 10^9$ L/mol, preferably at least $1 \times 10^{10}$ L/mol.

Preferably the non-human mammal is an ovine non-human mammal.

Ovine antibodies are antibodies which have been raised in a sheep. A number of advantages are associated with using sheep as production hosts for blood-derived antibodies that that bind to human TNFα. The inventors have found that the concentration of antibodies that bind to human TNFα present in the sheep blood (e.g. serum) remains substantially constant over time, typically taking around 6 months from obtaining a maximum concentration of specific antibodies for the concentration to halve. Thus, the need for frequent re-immunisation with human TNFα is avoided/minimised. Additionally, the substantially constant concentration of specific antibodies allows a high yield of blood-derived antibodies to be obtained per annum. In contrast, the inventors have found that the antibody yield per annum is far lower when using milk (e.g. bovine milk), eggs, or colostrum. Moreover, high concentrations of specific antibodies can be obtained at virtually any time point in the immunisation schedule (once maximum antibody concentrations have been reached). This is in contrast to other non-human mammals having fluctuating concentrations of specific antibodies in the blood, thus necessitating: measurement of the antibody concentration, and ensuring that a blood sample is obtained only when specific antibody concentrations are high. Therefore, using sheep as production hosts removes this additional step and/or removes unpredictability in the manufacturing method.

In addition, the present inventors have shown that specific blood-derived antibody concentrations between sheep is consistent.

Moreover, sheep are plentiful in the developed world, and easy to work with when compared to other non-human mammals.

Thus in one embodiment, a non-human mammal is a non-human mammal (e.g. ovine) that has a substantially constant blood concentration of polyclonal antibodies that bind to human TNFα after said non-human mammal has been administered an immunogen comprising human TNFα or a fragment thereof.

The term "substantially constant" as used in this context means that the blood concentration of polyclonal antibodies that bind to human TNFα decreases by 75% or less (preferably by 70%, 65%, or 60% or less, more preferably by 55% or less (e.g. 50% or less)) of the maximum blood concentration of said antibodies (100%) within and/or by 6 months (preferably within and by 6 months) after the maximum blood concentration of said antibodies has been reached.

Alternatively or additionally, the term "substantially constant" as used in this context may mean that within and/or by 6 months (preferably within and by 6 months) after the maximum blood concentration of polyclonal antibodies that bind to human TNFα has been reached (100%), the blood concentration of said polyclonal antibodies is at least 20% of the maximum, preferably at least 25%, 30%, 35%, or 40% or more preferably at least 45% (e.g. about 50%).

In one embodiment maximum blood concentration of polyclonal antibodies that bind to human TNFα occurs at at least 10 weeks from immunisation, such as at least 11 weeks from immunisation. Preferably the maximum blood concentration of polyclonal antibodies that bind to human TNFα occurs at about 12 weeks from immunisation.

Thus, the present invention includes a method for producing ovine antibodies for use in a composition of the invention, said method typically comprising:

i. administering an immunogen comprising a human TNFα or a fragment thereof to a sheep;
ii. allowing sufficient time for the generation of antibodies in the sheep; and
iii. obtaining the antibodies from the sheep.

The term "sheep" as used herein is synonymous with the term "ovine". As used herein, sheep comprise any species that fall within the *Ovis* genus (e.g. *Ovis ammon, Ovis orientalis aries, Ovis orientalis orientalis, Ovis orientalis vignei, Ovis Canadensis, Ovis dalli, Ovis nivicola*).

The term "ovine antibody" as used herein is an antibody that has at least 85%, 90%, 95%, or 99% amino acid sequence identity to an antibody that has been raised in a sheep. Preferably an "ovine antibody" as used herein is an antibody that has 100% amino acid sequence identity to an antibody that has been raised in a sheep.

In one embodiment a composition of the present invention comprises only ovine antibodies, and thus excludes antibodies from a non-ovine source.

The antibody is typically obtainable from the sheep serum. Thus, methods for producing ovine antibodies described herein generate sheep antisera comprising antibodies capable of binding to and/or neutralising human TNFα. In one embodiment an antibody is isolated and/or purified, for example isolated and/or purified from a sheep antiserum.

Preferably the non-human mammal is an equine non-human mammal.

Equine antibodies are antibodies which have been raised in a horse. Advantageously, a high yield of blood-derived antibodies that bind to human TNFα can be obtained per annum by using horses as production hosts. Moreover, equine blood cells have been found to settle rapidly upon collection of a sample, thus avoiding the need for a time-consuming centrifugation step when obtaining plasma.

In embodiments where the non-human mammal is an equine non-human mammal, the manufacturing method may comprise obtaining blood plasma from a blood sample and returning the blood cells from said sample to said equine non-human mammal. Suitably, the blood cells may be returned in less than 24 hours, less than 12 hours, less than 6 hours, less than 1 hour or less than 30 minutes after obtaining the blood sample.

Thus, the present invention includes a method for producing equine antibodies for use in a composition of the invention, said method typically comprising:
 i. administering an immunogen comprising a human TNFα or a fragment thereof to an equine;
 ii. allowing sufficient time for the generation of antibodies in the equine; and
 iii. obtaining the antibodies from the equine.

The term "horse" as used herein is synonymous with the term "equine". As used herein, horses comprise any species that fall within the *Equus* genus. Preferably a horse is one or more from the species *Equus ferus*, such as *Equus ferus caballus*.

The term "equine antibody" as used herein is an antibody that has at least 85%, 90%, 95%, or 99% amino acid sequence identity to an antibody that has been raised in a horse. Preferably an "equine antibody" as used herein is an antibody that has 100% amino acid sequence identity to an antibody that has been raised in a horse.

In one embodiment a composition of the present invention comprises only equine antibodies, and thus excludes antibodies from a non-equine source.

The antibody is typically obtainable from the horse blood plasma. Thus, methods for producing equine antibodies described herein generate equine blood plasma comprising antibodies capable of binding to and/or neutralising human TNFα. In one embodiment an antibody is isolated and/or purified, for example isolated and/or purified from an equine blood plasma.

The immunogen used to generate an antibody of the present invention is a human TNFα, which has optionally been purified. The term "human TNFα" as used herein encompasses a full-length human TNFα a variant thereof or a fragment thereof. Preferably the term "human TNFα" means a full-length human TNFα. Suitably, the human TNFα may be a recombinant human TNFα.

An immunogen may be a human TNFα comprising (or consisting of) SEQ ID No. 1. In one embodiment an immunogen is a fragment of SEQ ID No. 1. In one embodiment an immunogen is a human TNFα variant (or fragment thereof) having at least 70% (suitably at least 80%) sequence identity to SEQ ID No. 1. Suitably an immunogen is a human TNFα variant (or fragment thereof) having at least 90% (suitably at least 95%) sequence identity to SEQ ID No. 1.

An immunogen may be a human TNFα comprising (or consisting of) SEQ ID No. 2. In one embodiment an immunogen is a fragment of SEQ ID No. 2. In one embodiment an immunogen is a human TNFα variant (or fragment thereof) having at least 70% (suitably at least 80%) sequence identity to SEQ ID No. 2. Suitably an immunogen is a human TNFα variant (or fragment thereof) having at least 90% (suitably at least 95%) sequence identity to SEQ ID No. 2.

In one embodiment an immunogen comprises (or consists of) SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, or SEQ ID No. 13 or a sequence having at least 70% sequence identity thereto (for example at least 80% sequence identity thereto). In one embodiment an immunogen comprises (or consists of) a sequence having at least 90% (e.g. at least 95%) sequence identity to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12 or SEQ ID No. 13. In one embodiment an immunogen is a fragment or variant of one or more of said sequence(s).

In one embodiment a "variant" may be a mimic of the peptide or peptide fragment, which mimic reproduces at least one epitope of the peptide or peptide fragment. In another embodiment a "variant" may be a peptide or peptide fragment having at least one amino acid mutation or modification when compared to a sequence described herein. In one embodiment a variant is SEQ ID No. 13.

The "fragment" referred to herein may be a fragment of SEQ ID No. 1 having any number of amino acids from 1 to 156. Alternatively or additionally the "fragment" referred to herein may be a fragment of SEQ ID No. 2 having any number of amino acids from 1 to 232. The fragment preferably includes at least one epitope of human TNFα. The "fragment" may also have a common antigenic cross-reactivity and/or substantially the same in vivo biological activity as the human TNFα from which it is derived. For example, an antibody capable of binding to a fragment would also be capable of binding to the human TNFα from which it is derived. Alternatively, the fragment may share a common ability to induce a "recall response" of a T-lymphocyte which has been previously exposed to an antigenic component of human TNFα.

In one embodiment a fragment comprises (or consists of) SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, or SEQ ID No. 12 or a sequence having at least 70% sequence identity thereto (for example at least 80% sequence identity thereto). In one embodiment a fragment comprises (or consists of) a sequence having at least 90% (e.g. at least 95%) sequence identity to SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, or SEQ ID No. 12.

In one embodiment an immunogen or fragment thereof comprises (or consists of) the N-terminal or N-terminal fragment of human TNFα (e.g. SEQ ID No. 1 or SEQ ID No. 2). In one embodiment the N-terminal or N-terminal fragment comprises (or consist of) SEQ ID No. 3, SEQ ID No. 4, SEQ ID No. 5, SEQ ID No. 6 or SEQ ID No. 7 or a sequence having at least 70% sequence identity thereto (for example at least 80% sequence identity thereto). In one embodiment the N-terminal or N-terminal fragment comprises (or consists of) a sequence having at least 90% (e.g. at least 95%) sequence identity to SEQ ID No. 3, SEQ ID No. 4, SEQ ID No. 5, SEQ ID No. 6 or SEQ ID No. 7.

In some embodiments the polyclonal antibodies of the invention exhibit cross-reactivity to and/or neutralisation of murine TNFα.

Advantageously, antibodies binding to N-terminal fragments of human TNFα may exhibit improved neutralisation properties.

Without wishing to be bound by theory, it is believed that human TNFα comprises (or consists of) a plurality of epitopes. For example a human TNFα monomer may comprise at least 2 or 3 epitopes. Human TNFα is also believed to adopt a trimeric structure. Thus, a human TNFα trimer may comprise further epitopes. Without wishing to be bound by theory, it is believed that at least 5 to 15 antibodies (e.g. 10 to 15 antibodies) of the composition may bind to a human TNFα trimer. Suitably about 12 antibodies of the composition may bind to a human TNFα trimer.

The antibody composition of the invention comprises polyclonal antibodies, thus preferably said antibody composition comprises a population of antibodies wherein the population is capable of binding to multiple epitopes (preferably all epitopes) of human TNFα.

In one embodiment an antibody composition of the invention comprises a first antibody that binds to a first epitope of human TNFα and a second antibody that binds to a second epitope of human TNFα. Preferably, an antibody composition of the invention comprises a third antibody that binds to a third epitope of human TNFα. Suitably, an antibody composition of the invention may comprise further antibodies, each of which bind to different further epitopes of human TNFα.

An antibody composition of the invention suitably comprises antibodies that bind to SEQ ID No. 1 and/or SEQ ID No. 2. Suitably an antibody composition of the invention may comprise antibodies that bind to SEQ ID No. 13.

In one embodiment an antibody composition comprises antibodies that bind to one or more of (e.g. a plurality of) SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12 or SEQ ID No. 13, or a sequence having at least 70% sequence identity thereto (for example at least 80% sequence identity thereto). In one embodiment an antibody composition comprises antibodies that bind to one or more (e.g. a plurality of) sequence(s) having at least 90% (e.g. at least 95%) sequence identity to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12 or SEQ ID No. 13.

In one embodiment an antibody composition comprises antibodies that bind to the N-terminal of human TNFα (e.g. SEQ ID No. 1 or SEQ ID No. 2). In one embodiment said antibodies bind to one or more of (e.g. a plurality of) SEQ ID No. 3, SEQ ID No. 4, SEQ ID No. 5, SEQ ID No. 6 or SEQ ID No. 7 or a sequence having at least 70% sequence identity thereto (for example at least 80% sequence identity thereto). In one embodiment said antibodies bind to one or more (e.g. a plurality of) sequence(s) having at least 90% (e.g. at least 95%) sequence identity to SEQ ID No. 3, SEQ ID No. 4, SEQ ID No. 5, SEQ ID No. 6 or SEQ ID No. 7.

A plurality of sequences means at least 2 (e.g. at least 3, 4, 5, 6, 7, 8, 9, 10, 11 or 12) of said sequences. Suitably the term plurality of sequences means all of the recited sequences.

Antigens may be formulated with an adjuvant. Suitable adjuvants may include alum (aluminium phosphate or aluminium hydroxide), saponin (and its purified component Quil A), Freund's complete and incomplete adjuvant, RIBBI adjuvant, and other adjuvants used in research and veterinary applications.

The invention contemplates a wide variety of immunisation schedules. In one embodiment, a non-human mammal (e.g. a sheep or horse) is administered an immunogen on day zero and subsequently receives an immunogen at intervals thereafter. The interval range and dosage range required can be determined by the person skilled in the art based on inter alia the precise nature of the immunogen, the route of administration, and the nature of the formulation. Variations in these dosage levels can be adjusted using standard empirical optimisation routines. Similarly, it is not intended that the present invention be limited to any particular schedule for antibody collection. The collection time may be typically after day 56. Levels of the specific antibody, i.e. that which binds to the immunogen, may represent at least 2 g per litre of blood, serum or plasma (e.g. at least 3 g per litre of blood, serum or plasma).

The antibodies obtained from the non-human mammal (e.g. sheep or horse) may be subsequently purified thus providing a "purified fraction" as referred to herein. In one embodiment the antibodies may be purified by precipitation, chromatography, filtration, or combinations thereof. The purification method chosen may be one that enables IgG to remain in solution, co-isolate an inhibitor (e.g. al-antitrypsin), co-isolate albumin, or combinations thereof.

The precipitation may be a sodium sulphate precipitation, or a caprylic acid precipitation. Suitably, the precipitation is a sodium sulphate precipitation. Advantageously, sodium sulphate precipitation allows for co-isolation of al-antitrypsin.

The intact polyclonal antibody of the invention is suitably formulated with a buffer. The buffer may include physiological salts such as sodium citrate and/or citric acid. A physiological salt may be present in the buffer at a concentration of 100-200 mM or 125-175 mM. Suitably a physiological salt may be present in a buffer at a concentration of approximately 150 mM (preferably at 153 mM).

The antibody composition of the invention is formulated for oral administration. Orally administered antibody compositions of the invention have been found to be associated with one or more of the following unexpected advantages:

efficacious concentrations of the antibodies reach the desired area of the gastrointestinal tract more rapidly when administered orally compared to antibody formulations administered intravenously and, especially, subcutaneously or intramuscularly;

a large proportion of the polyclonal antibodies reach their target, therefore allowing for administration of significantly lower concentrations (e.g. less than 10%), e.g. when compared with systemic administration where most antibodies remain in the blood and extracellular fluid compartment of the body;

orally administered polyclonal antibodies are believed to be confined to the lumen and wall of the gastrointestinal tract with none entering the systemic circulation. This has three major advantages: i. oral administration does not evoke a systemic immune response so that administration with compositions of the invention can be continued indefinitely without evoking a humoral immune response; ii. for the same reason there is no risk of acute or delayed hypersensitivity reactions; and iii. the polyclonal antibodies of the invention will not neutralise systemically located TNFα, thereby avoiding the risk of infections such as tuberculosis, and other complications, including malignancy;

oral products receive much less regulatory scrutiny. Indeed, the consumption of e.g. horse, sheep, or ox plasma as a nutritional supplement drink provides further testament as to its safety when orally administered. Furthermore, some oral antibody-based products are treated as a food;

antibodies for oral administration require less purification and safety testing than those given systemically;

manufacture does not require the use of clean room facilities;

cost of therapy is reduced significantly for reasons including: the relatively low manufacturing costs of the polyclonal antibodies of the invention; the lower concentrations of antibodies required when administering orally; avoiding the need for admission to hospital as day cases; and avoiding the need for nurse/healthcare professional time as is required for systemic (e.g. IV) administration; and/or oral formulation provides for improved patient convenience, allowing administration from at the subject's own home and at a time convenient to him/her. Also, the majority of subjects, especially the paediatric group, find a pleasantly-flavoured oral product more acceptable than one administered systemically.

Compositions suitable for oral delivery may be in the form of solutions, suspensions or dry powders which are dissolved or suspended in a suitable vehicle prior to use.

In preparing pharmaceutical formulations, the antibodies can be dissolved in the vehicle, and sterilised for example by filtration through a sterile filter using aseptic techniques before filling into suitable sterile vials or ampoules and sealing. Advantageously additives such as buffering, solubilising, stabilising, preservative or bactericidal or suspending and/or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The containers are sealed aseptically.

In a particularly preferred embodiment, a composition for oral administration is formulated as a liquid.

A problem with oral administration is ensuring that a sufficient concentration of functional antibody is transported through the gastrointestinal tract to its target (e.g. the small intestine or the colon). Factors that may inhibit optimal amounts of functional antibody reaching the gut include the proteolytic enzymes present in the digestive secretions, which degrade the antibody molecule. Thus, the antibody composition of the invention comprises means for protecting the antibodies during gastrointestinal transit. Such means counter and/or reduce the undesirable effects that are encountered by the antibody composition during transit. Undesirable effects may be attributable to for example gastrointestinal enzymes (e.g. stomach enzymes such as pepsin) and the chemical environment (e.g. stomach acid).

The term "means for protecting the antibodies during gastrointestinal transit" as used herein is not intended to encompass a protective/stabilising amino acid modification (e.g. point mutation, substitution, addition, or deletion) of the antibody polypeptide itself or a protective/stabilising post-translational modification of the antibody (e.g. glycosylation). However, as an exception, in one embodiment the means may include a PEGylation moiety covalently attached to an antibody of the invention, while in an alternative embodiment PEGylation and PEGylation moieties are also excluded. In fact, methods for protecting/stabilising an antibody by way of amino acid modification and post-translational modification are disadvantageous, as they complicate the manufacturing process and increase production costs. For the avoidance of doubt, the foregoing does not exclude the presence of protective/stabilising amino acid modifications of the antibody polypeptide or protective/stabilising post-translational modifications of the antibody in addition to the presence of a means for protecting the antibodies during gastrointestinal transit as described herein.

Preferably the means for protecting the antibodies does not comprise a lectin. More preferably, the means for protecting the antibodies is not complexed with an antibody of the invention.

There follows a non-limiting description of a variety of embodiments of said means. Each of said embodiments may be employed alone or in combination with each other. Additional means known to a skilled person are encompassed by the present invention, and may also be employed alone or in combination with any of the following embodiments.

In a particularly preferred embodiment the means for protecting the antibodies described herein comprises at least a protease inhibitor. Advantageously, the present inventors have discovered that a composition comprising blood-derived polyclonal antibodies that bind to a human tumour necrosis factor α (TNFα) and a protease inhibitor exhibits unexpected synergistic effects when treating an inflammatory disorder (i.e. more than the expected additive effects obtained from observations of treating a subject with an antibody and a protease inhibitor alone).

Without wishing to be bound by theory, it is believed that the epithelial surface of the gastrointestinal tract in subjects with inflammatory disorders loses its normal layer of protective mucus. The present inventors have found that this loss leads to attack of said epithelial surface by proteolytic enzymes resulting in homeostatic disruption and/or continued/worsened pathology. The antibody composition of the present invention surprisingly allows both protection of the gastrointestinal tract from said proteolytic enzymes as well as a reduction in inflammation and treatment of other symptoms by way of TNFα binding.

While (as described below) any protease inhibitors can be used in the present invention, in one embodiment the protease inhibitor is a soybean-derived protease inhibitor.

Protease inhibitors selected from the Bowman-Birk inhibitor family of proteins are particularly preferred. The Bowman-Birk inhibitors are serine protease inhibitors that interact with and inhibit proteases by way of an exposed surface loop, which is typically a disulphide-linked short beta-sheet region. Suitable Bowman-Birk inhibitors can be obtained from multiple sources, including legumes (e.g. soybean, lima beans, mung beans, broad beans, adzuki bean), wheat (e.g. *Triticum aestivum*), barley (e.g. *Hordeum vulgare*), rice (e.g. *Oryza sativa*), nuts (e.g. *Arachis hypogaea*), *Coix lachryma jobi, Setaria italica, Macrotyloma axillaris, Lonchocarpus carpassa, Vicia angustifolia*, and Alfalfa. Suitably, a Bowman-Birk inhibitor may be obtained from a seed of one or more of said sources.

In one embodiment a means for protecting the antibodies of the composition during gastrointestinal transit comprises a polypeptide which binds specifically to and suppresses or inactivates the proteolytic activity of trypsin and/or chymotrypsin. Such means may be an inhibitor of trypsin-1 and/or trypsin-2. Alternatively or additionally said means may be an inhibitor of chymotrypsin B.

In one embodiment, said inhibitor is a macromolecular inhibitor (e.g. a macromolecular inhibitor having a molecular weight of at least 5 kDa), such as a polypeptide-based inhibitor. By way of example, said inhibitor(s) may contain a polypeptide loop, which when cleaved by either trypsin or chymotrypsin causes the inhibitor to bind very strongly to the protease thus inhibiting the further action of trypsin and/or chymotrypsin.

In one embodiment a means for protecting an antibody during gastrointestinal transit comprises a means obtainable from an egg, such as a hen (chicken) egg. More specifically, a means for protecting an antibody during gastrointestinal transit may be an egg white. Suitably, the egg white may be a powdered egg white. Thus, in one embodiment the present invention comprises admixing an intact polyclonal antibody with an egg (suitably an egg white, preferably a powdered egg white).

A means obtainable from an egg (e.g. egg white), may be a trypsin inhibitor, a chymotrypsin inhibitor or a combination thereof. Thus, the means may comprise an egg-derived (e.g. egg white-derived) trypsin and/or chymotrypsin inhibitor.

In one embodiment the means present in the egg (e.g. egg white) is one or more of ovomucoid, ovostatin, ovomacroglobulin, or combinations thereof. Ovomucoids (Mw 28,500±3,500) are glycoprotein protease inhibitors of avian egg white. Said inhibitors have activity when tested against bovine trypsin and chymotrypsin. Ovostatins and ovomacroglobulins are protease inhibitors found in raw avian egg white.

The means obtainable from an egg may be used at any suitable concentration. Where the means is a dried egg (e.g. powdered egg white), said dried egg may be present in the composition at a concentration of at least 25 g/L or at least 35 g/L. In one embodiment the dried egg may be present in the composition at a concentration of at least 45 g/L or at least 55 g/L. In some embodiments the dried egg may be present in the composition at a concentration of between 40 g/L to 80 g/L (suitably between 50 g/L to 70 g/L).

In one embodiment a means for protecting an antibody during gastrointestinal transit comprises α-1-anti-trypsin.

In another embodiment the means is a soybean trypsin inhibitor.

In one embodiment, an inhibitor cocktail may be provided, for convenience, in the form of colostrum (e.g. bovine). Alternatively (or in addition), the active component(s) thereof may be employed. Colostrum is readily combinable with antibodies to provide a suitable formulation for oral administration.

In one embodiment, the trypsin inhibitor is a small protein (e.g. Mw 5-25 kDa) that is naturally synthesized in the exocrine pancreas which prevents conversion of trypsinogen to trypsin, so protecting itself against trypsin digestion. Pancreatic trypsin inhibitor competitively binds to the active site of trypsin and inactivates it at a very low concentration. Examples of trypsin inhibitors suitable for use in the present invention include both naturally produced and recombinantly-produced molecules, such as:

by Kunitz (1945) is one of several trypsin inhibitors found in soybeans. The best known preparation is that of Kunitz (Mw 21,500±800; isoelectric point: 4.5). The Kunitz soybean inhibitor consists of a single polypeptide chain cross-linked by two disulfide bridges, and inhibits trypsin mole-for-mole and to a lesser extent chymotrypsin. Lima bean trypsin inhibitor (LBI) acts upon both trypsin and chymotrypsin by forming equimolar complexes. The trypsin susceptible binding site is a Lys-Ser peptide bond, whereas the site of chymotrypsin action is a Leu-Ser bond (Krahn and Stevens 1970). Lima bean trypsin inhibitors (Mw 8,000-10,000) may be chromatographically separated into as many as six variants. All have similar but not identical amino acid composition, contain six or seven disulphide bonds and lack methionine and tryptophan.

By way of further example, Bowman Birk protease inhibitors are a group of chymotrypsin and trypsin inhibitors produced by Soybeans and a range of leguminous plants. They are small disulphide rich proteins of 7-10 kda which are non-toxic to humans and well tolerated. Chymotrypsin peptide inhibitors which are extremely stable to extremes of pH occur in turtle egg whites. These small peptide inhibitors (approx 13 kDa) form stable complexes with chymotrypsin (Guha et al (1984) J. Bioscience 6: 155-163).

In one embodiment, the trypsin and/or chymotrypsin inhibitor(s) component may be an antibody (including a fragment thereof) that binds to (e.g. specifically binds to) and inactivates the enzymatic activity of trypsin and/or chymotrypsin. Such antibody-based inhibitors may be used as an alternative or in addition to the above non-antibody-based inhibitors. Thus, an inhibitor combination of an antibody-based inhibitor and a non-antibody inhibitor may be employed. By way of example, a non-antibody inhibitor (e.g. an egg-white derived inhibitor) may be used in combination with an antibody inhibitor where the antibody inhibits chymotrypsin (and/or trypsin). Similarly, a non-antibody chymotrypsin inhibitor may be used in combination with an antibody inhibitor where the antibody inhibits trypsin (and/or chymotrypsin). Such antibodies may be prepared routinely.

In one embodiment a trypsin and/or chymotrypsin inhibitor may be present in the composition at a concentration of at least 25 g/L or at least 35 g/L. In one embodiment a trypsin and/or chymotrypsin inhibitor may be present in the

| Source | Mw | Additional information |
| --- | --- | --- |
| Lima beans | 8-10 kDa | There are six different lima bean inhibitors. |
| Bovine pancreas | 6.5 kDa | Kunitz inhibitor is the best known pancreatic inhibitor. Chymotrypsin is also inhibited by this chemical, but less tightly. When extracted from lung tissue, this is known as aprotinin. |
| Ovomucoid | ca. 27 kDa | Ovomucoids are glycoprotein protease inhibitors found in raw avian egg white. |
| Ovostatin | ca. 175 kDa | Ovostatins (ovomacroglobulins) are protease inhibitors found in raw avian egg white. |
| Soybeans | 20.7-22.3 kDa | Soybeans contain several trypsin inhibitors. All also bind to and inactivate chymotrypsin. |

Natural pancreatic trypsin inhibitors are produced by the acinar cells and provide security against accidental trypsinogen activation and consequential unbridled proteolysis. By way of example, the intracellular basic trypsin inhibitor (BPTI) was first crystallized by Kunitz and Northrop in 1936. Basic pancreatic trypsin inhibitor (BPTI) forms a very stable 1:1 complex with bovine trypsin between pH 3 and 10, and also human trypsins. Chymotrypsin is also inhibited by BPTI. Soybean trypsin inhibitor (SBTI) first crystallized composition at a concentration of at least 45 g/L or at least 55 g/L. In some embodiments a trypsin and/or chymotrypsin inhibitor may be present in the composition at a concentration of between 40 g/L to 80 g/L (suitably between 50 g/L to 70 g/L).

Alternatively or additionally (preferably additionally) a means for protecting an antibody during gastrointestinal transit comprises an antacid. In use, said antacid component helps protect the antibody component from the highly acid gastric environment that exists within a subject.

An antacid is any substance, generally a base or basic salt, which counteracts stomach acidity. In other words, antacids are stomach acid neutralizers that raise the stomach pH, ideally above pH 5.0, for a limited time period. Antacids perform a neutralization reaction, i.e. they buffer gastric acid, raising the pH to reduce acidity in the stomach.

Examples of suitable antacids for use in the present invention include: aluminium hydroxide (eg. Amphojel, AlternaGEL); magnesium hydroxide (e.g. Phillips' Milk of Magnesia); aluminum hydroxide with magnesium hydroxide (e.g. Maalox, Mylanta, Diovol); aluminium carbonate gel (eg. Basaljel); calcium carbonate (eg. Alcalak, TUMS, Quick-Eze, Rennie, Titralac, Rolaids); sodium bicarbonate (eg. bicarbonate of soda, Alka-Seltzer); magnesium carbonate; magnesium trisilicate; hydrotalcite (eg. $Mg_6Al_2(CO_3)(OH)_{16}.4(H_2O)$; Talcid); bismuth subsalicylate (e.g. Pepto-Bismol); alginates (e.g. sodium alginate, alginic acid); magaldrate with simethicone (eg. Pepsil); any of the above in combination with simethicone for example Asilone, which has three active ingredients, aluminium hydroxide and magnesium oxide neutralise the acid removing the cause of the pain, and dimethicone.

In one embodiment the antacid is magnesium hydroxide and/or aluminium hydroxide. The aluminium hydroxide may be added to the composition in the form of a dried aluminium hydroxide gel. Preferably a composition of the invention comprises magnesium hydroxide and aluminium hydroxide.

The antacid may be used at any suitable concentration. In one embodiment an antacid may be present at a concentration of at least 5 g/L or at least 10 g/L (e.g. per antacid used). In another embodiment an antacid may be present at a concentration of at least 15 g/L or at least 20 g/L (e.g. per antacid used). In some embodiments between 5 g/L to 40 g/L (suitably between 10 g/L to 30 g/L) of antacid may be used (e.g. per antacid used).

In a preferred embodiment a composition of the invention comprises 5 g/L to 40 g/L (suitably between 10 g/L to 30 g/L) of magnesium chloride and/or 5 g/L to 40 g/L (suitably between 10 g/L to 30 g/L) of aluminium hydroxide.

In one embodiment an antibody composition comprises an antacid molecule and: a polypeptide which binds specifically to and suppresses or inactivates the proteolytic activity of trypsin and/or chymotrypsin; and/or an antibody that binds to trypsin and/or chymotrypsin and inactivates the protease activity of said trypsin and/or chymotrypsin.

A composition of the invention may comprise one or more antimicrobial. In one embodiment an antimicrobial is methylparaben (E218) and/or propylparaben (E216). Suitably, a composition of the invention comprises a combination of methylparaben (E218) and propylparaben (E216).

An antimicrobial (e.g. each antimicrobial) may be present in the composition at a concentration of at least 0.2 g/L or at least 0.4 g/L. In one embodiment an antimicrobial is present in the composition at a concentration of at least 0.6 g/L or at least 1.0 g/L. Suitably, an antimicrobial may be present at a concentration of at least 1.5 g/L or at least 2.0 g/L. In some embodiments the antimicrobial is present at a concentration between 0.2 g/L to 1.0 g/L. In other embodiments the antimicrobial is present at a concentration between 1.0 g/L to 3.0 g/L (e.g. 1.5 g/L to 2.5 g/L).

A composition of the invention may comprise a suspension stability agent, for example glycine. The suspension stability agent (e.g. 200 mM glycine) may be present at a concentration of at least 5 g/L, or at least 10 g/L. In other embodiments the suspension stability agent (e.g. 200 mM glycine) is present at a concentration between 10 g/L to 20 g/L.

Alternatively or additionally, a composition of the invention may comprise an antifoaming agent, such as simethicone. Said antifoaming agent may be present at a concentration of at least 5 g/L, or at least 10 g/L. In one embodiment the antifoaming agent is present at a concentration of between 5 g/L and 25 g/L (suitably between 10 g/L and 20 g/L).

In addition to the above a composition of the invention may comprise sweeteners and/or flavourants, such as vanilla essence, a sugar (e.g. glucose, sucrose, etc.), sugar alcohols, honey, fruit, syrups (e.g. maple syrup, rice syrup, birch syrup, pine syrup, hickory syrup, poplar syrup, palm syrup, sugar beet syrup, sorghum syrup, corn syrup, cane syrup, golden syrup, barley malt syrup, molasses (treacle), brown rice syrup, agave syrup, yacon syrup), acesulfame potassium (also known as Sunett), alitame (also known as aclame), aspartame (also known as Equal or Nutrasweet), anethole, cyclamate, glycyrrhizin, lo han guo, neotame, perillartine, saccharin (also known as Sweet 'n' Low), stevioside, sucralose (also known as SucraPlus and Splenda), or inulin. In one embodiment the sweeteners include sodium saccharin and mannitol. In one embodiment the flavourant includes peppermint oil.

Sweeteners and/or flavourants may be present in a composition of the invention at a concentration of between 0.1 g/L to 40 g/L, for example 0.1 g/L to 30 g/L.

The composition of the invention may comprise a suspending agent, such as xantham gum. Said suspending agent may be present at a concentration of at least 1 g/L or 2 g/L. Suitably, said suspending agent may be present at a concentration between 1 g/L to 10 g/L, for example 3 g/L to 5 g/L.

In one embodiment a composition of the invention may be formulated as per the table below:

|  | Category | Material name | Concentration |
|---|---|---|---|
| Active components | IgG | Intact polyclonal antibody (e.g. ovine or equine polyclonal antibody) that binds human TNFα | 25-100 g/l |
|  | Protease inhibitor | Egg white dried (EWD) | 40-100 g/l |
| Excipients | Antacid | Magnesium hydroxide | 10-35 g/l |
|  |  | Aluminium hydroxide | 10-35 g/l |

Optionally, the composition may further comprise:

| Category | Material name | Concentration |
|---|---|---|
| Antimicrobial | Methylparaben (E218) | 0.5-5 g/l |
|  | Propylparaben (E216) | 0.1-1.2 g/l |
| Suspension stability | Glycine (200 mM) | 5-25 g/l |
| Antifoaming agent | Simethicone | 5-25 g/l |
| Sweeteners | Sodium saccharin | 0.1-0.8 g/l |
|  | Mannitol | 10-30 g/l |
| Flavour | Peppermint oil | 0.1-0.5 g/l |
| Suspending agent | Xanthan gum | 1-10 g/l |

In a preferred embodiment, a composition of the invention may be formulated as per the table below:

| Category | | Material name | Concentration |
|---|---|---|---|
| Active components | IgG | Intact polyclonal antibody (e.g. ovine or equine polyclonal antibody) that binds human TNFα | 50 g/l |
| | Protease inhibitor | Egg white dried (EWD) | 60 g/l |
| Excipients | Antacid | Magnesium hydroxide | 23.4 g/l |
| | | Aluminium hydroxide (e.g. as a dried gel) | 26.4 g/l |

In a preferred embodiment, a composition of the invention may optionally further comprise:

| Category | Material name | Concentration |
|---|---|---|
| Antimicrobial | Methylparaben (E218) | 2 g/l |
| | Propylparaben (E216) | 0.6 g/l |
| Suspension stability | Glycine (200 mM) | 15 g/l |
| Antifoaming agent | Simethicone | 16.89 g/l |
| Sweeteners | Sodium saccharin | 0.4 g/l |
| | Mannitol | 21 g/l |
| Flavour | Peppermint oil | 0.2 g/l |
| Suspending agent | Xanthan gum | 4 g/l |

In addition (or alternatively) to the above-described formulation components, the composition may include a physical and/or chemical means for protecting the antibody from the acidic environment of the stomach so that an active antibody is ultimately delivered to the intestinal site of action (e.g. the colon).

By way of example, the antibodies may be encapsulated (e.g. pellets, granular matrices, beads, microspheres, nanoparticles, or liposomes) and/or may be chemically protected (e.g. by PEGylation).

Conventional encapsulation techniques suitable for use in the present invention include:

| Technique employed | Polymer(s) used |
|---|---|
| pH dependent | Eudragit L100 and S100 |
| | Eudragit L100 and S100 |
| | Eudragit L100 and S100 |
| | Eudragit S, Eudragit FS, Eudragit P4135 F |
| | Eudragit L 30 D-55 and Eudragit FS 30 D |
| Time dependent | Hydroxy propyl methyl cellulose |
| | Hydroxyethyl cellulose, ethyl cellulose, microcrystalline cellulose |
| | Lactose/behinic acid |
| | Hydroxy propyl methyl cellulose |
| | Hydroxy propyl methyl cellulose acetate succinate |
| Bacteria dependent/ Polysaccharide based | Chitosan |
| | Pectin |
| | Guar gum |
| | Chondroitin sulphate |
| | Amylose |
| | Alginates |

The pH in the terminal ileum and colon (except ascending colon) is higher than in any other region of the gastrointestinal (GI) tract. Thus a dosage form that disintegrates preferentially at high pH levels is optimal for site-specific delivery into this region. One of the simplest approaches for designing a pH-dependent multiparticulate colon-specific delivery system is enteric coated granules. Enteric coating has traditionally been used to prevent drug release in the upper GI tract. Enteric coating polymers may be used as both binders and as coating materials for granules. The incorporation of citric acid into the coating and/or the tablet matrix helps to retard in vitro release and in vivo absorption because of the prolongation in disintegration time of the core system due to the presence of the acid. Most commonly used pH-dependent coating polymers for peroral delivery are methacrylic acid copolymers, Eudragit L100 and Eudragit S100, which dissolve at pH 6.0 and 7.0 respectively. The combination of these two polymers in various ratios makes it possible to manipulate drug release within 6.0-7.0 pH range. Capsules comprising these polymers may be further coated with solutions of polymethacrylates.

Similarly, excipients such as aqueous hydroxypropyl methyl cellulose acetate succinate as a coating material and citric acid as a pH regulating agent may be added. Glyceryl palmitostearate may be used as a retardant material to formulate controlled release matrices.

Coating formulations (e.g. Eudragit S100) may be further covered with a layer of chitosan HCl. Upon hydration, the capsule shell dissolves and the chitosan layer forms a gel (internal pH of 4.5), which generates an acidic environment around the Eudragit film so that it does not dissolve in the ascending colon. In the ascending colon, the chitosan HCl gel is degraded by the colonic micro flora, thereby exposing the Eudragit film to the colonic environment. But since the ascending colon is weakly acidic with a pH is less than 7.0, the film coat still remains intact. However, on arrival in the descending colon where pH is greater than 7, the Eudragit film coat dissolves and the drug is released in a controlled fashion from the matrices. Multi-layer coats may be employed based on, for example, an inner coat (a combination of Eudragit RL/RS), and an outer coat (Eudragit FS 30D). Eudragit FS 30D is an-ionic co-polymer of methyl acrylate, methyl methacrylate and methacrylic acid and is pH sensitive and dissolves at pH above 6.5.

Microbially-controlled delivery systems may also be employed, which rely on the unique enzymatic ability of the colonic micro flora. Delivery systems of this type enable a more specific targeting, independent of pH variations along the GI tract. Many natural polysaccharides such as chondroitin sulphate, pectin, dextran, guar gum etc. may be employed. Multiparticulate systems comprising hydrogel beads (chitosan and tripolyphosphate (TPP)) are one option—TPP acts as a counter ion to positively charged chitosan to form gel beads. The beads are loaded with bovine serum albumin (BSA), a protein that is liable to degradation in the upper parts of GI tract, and the cross-linking of chitosan with TPP results in reduced solubility of chitosan, thereby resulting in lesser protein (antibody) release during upper GI transit. Amylose is a particularly good film-forming polymer (via gelation), and may also be mixed with Eudragit RS/RL 30D aqueous dispersions. Similarly, amidated low methoxy pectin which forms rigid gels with divalent cations (e.g. calcium or zinc) may be employed to produce calcium pectinate gel beads for colonic delivery. Pectin may be combined with calcium salts—calcium pectinate (the insoluble salt of pectin) is not degraded by gastric or intestinal enzymes but is capable of degradation by colonic pectinolytic enzymes. As an alternative to crosslinking of soluble polysaccharides to form insoluble salts, the polysaccharide based system may be coated with pH sensitive polymers. By way of example, chitosan microcores may be prepared and coated with acrylic polymers, such as Eudragit L100 and Eudragit S100 respectively. Eudragit P-4135 F represents a further example of a suitable pH-sensitive polymer, which may be employed to prepare microparticles for colonic delivery.

Multiparticulate systems may be employed, which combine pH sensitive delivery and biodegradation in the colonic environment. By way of example, an inner entrapment matrix of chitosan microcores may be prepared using a technique such as spray drying, followed by application of chitosan microcores microencapsulated within Eudragit polymers by a technique such as oil-in oil solvent evaporation. Upon dissolution of the outer Eudragit coat at appropriate pH the exposed chitosan microcores swell and form a gel barrier in alkaline pH, and, in the colonic region, the chitosan undergoes degradation thereby enhancing release. Similar colonic delivery multiparticulate systems may be based on chitosan microspheres coated with Eudragit L100 or S100. Suitable preparation techniques include emulsion solvent evaporation. The chitosan may be cross-linked with glutaraldehyde.

Polyacrylates represent a further example of a suitable delivery vehicle for use in the present invention. By way of example, a terpolymer of styrene and hydroxyethyl methacrylate cross-linked with a difunctional azo-compound may be employed. The system depends on cleavage of the azo bond by colonic microflora resulting in degradation of polymer. Similarly, a pH responsive poly (methacrylic-g-ethylene glycol) hydrogel may be employed as an oral delivery vehicle. Once inside the basic and neutral environment of the small intestine, the gels rapidly swell and dissociate.

In another embodiment, a microcapsule formulation may be employed for peroral colon-specific delivery. In more detail, aqueous colloidal terpolymers of ethylacrylate/methyl methacrylate/2-hydroxyl ethyl methacrylate (poly (EA/MME/HEMA), for example as synthesized by emulsion polymerization technique(s) may be employed. These polymers exhibit delayed release profiles which were characterized by a long lag time and subsequent rapid release of the entrapped moiety.

In another embodiment, orally administered nanoparticles may serve as suitable delivery vehicles. By way of example, loaded nanoparticles may be entrapped into pH sensitive microspheres, which serve to deliver the incorporated nanoparticle to the desired colonic site of action. Nanoparticles have a large specific surface, which is indicative of high interactive potential with biological surfaces. Thus, bioadhesion can be induced by binding nanoparticles with different molecules. By way of example, nanoparticles may be prepared from gliadin protein isolate from wheat gluten and then conjugated with lectins (glycoproteins of non-immune origin which provide specific bioadhesion). Accordingly, nanoparticles are provided, which have a high capacity for non-specific interaction with intestine and the binding of lectin provided greater specificity for colonic mucosa.

In one embodiment, a delivery vehicle based on an albumin-chitosan mixed matrix microsphere-filled coated capsule formulation may be employed. In this regard, an antibody preparation of the invention is filled into hard gelatin capsules and enteric coated.

In one embodiment, albumin microspheres may be employed as the oral delivery system.

In one embodiment, squalane oil-containing multiple emulsions may be employed

In one embodiment, poly(lactide-co-glycolide) microspheres may be employed as the oral delivery vehicle.

In one embodiment, a colonic delivery coating comprising a mixture of pH-responsive enteric polymer (Eudragit S) and biodegradable polysaccharide (resistant starch) in a single layer matrix film may be employed. Examples of these delivery vehicles are available commercially, such as from Encap Drug Delivery (Livingston, UK)—particular embodiments include PHLORAL™ and ENCODE™.

In addition (or alternatively) to the above delivery vehicle embodiment, the antibodies of the present invention may be protected from acid erosion by PEGylation with polyethylene glycol (PEG). PEG of various molecular weights (500-40000 Da) may be coupled to IgG, for example, in a ratio of 2-20 PEG molecules per antibody molecule. We refer to Greenwald, R. B et al (2003) "Effective drug delivery by PEGylated drug conjugates", Advanced Drug Delivery Reviews 55, pp. 217-250. This publication is incorporated in its entirety by reference thereto.

In one embodiment, delivery capsules such as liposomes, micro- or nanocapsules (eg. chitosan nanocapsules) may be chemically modified with poly(ethylene glycol) (PEG). The typical degree of PEGylation is in the range of 0.1% to 5%, such as 0.5% to 2%, for example 0.5% or 1%. The presence of PEG, whether alone or grafted to chitosan, improves the stability of the delivery capsules in the gastrointestinal fluids.

In one embodiment, the antibodies of the present invention may be treated with monomethoxypoly(ethylene) glycols activated by cyanuric chloride, succinimidyl succinate, and tresyl chloride.

PEGylated delivery vehicles such as liposomes, micro- or nanocapsules have an intrinsic ability to accumulate at disease sites and facilitate transfection of target cells. Unlike many viral vectors, PEGylated liposomes are generally considered to be non-immunogenic.

In one embodiment, a branched PEGylating reagent is employed as branched PEG protecting groups are more effective than linear PEG molecules.

In one aspect the invention provides an antibody composition of the invention for use in treating an inflammatory disorder, wherein the antibody composition is orally administered to a subject. There is also provided a related use of the antibody composition in the manufacture of a medicament for treating an inflammatory disorder, as well as methods of treating an inflammatory disorder comprising orally administering an antibody composition of the invention to a subject.

The term "disorder" as used herein also encompasses a "disease". In one embodiment the disorder is a disease.

The term "subject" as used herein refers to a mammal, such as a human or other animal. Preferably "subject" means a human subject.

A means for protecting an antibody during gastrointestinal transit may be orally administered sequentially (e.g. as separate components) or simultaneously with an antibody of the invention. When the administration is sequential, preferably the means for protecting is administered prior to an antibody of the invention. In a preferred embodiment a means for protecting is administered simultaneously with an antibody of the invention.

An antibody composition according to the present invention may be used to treat an inflammatory disorder selected from: septic shock, a gastrointestinal disorder (such as an intestinal disorder), an inflammatory bowel disease, a graft vs. host disorder, and/or an inflammatory disorder caused/exacerbated by: intestinal infection, non-steroidal anti-inflammatory drugs, stress, alcohol, bowel surgery, ischaemia and reperfusion, food allergy, or combinations thereof.

In a preferred embodiment the inflammatory disorder is an inflammatory bowel disease selected from ulcerative colitis, Crohn's disease, or a combination thereof In a particularly preferred embodiment the inflammatory disorder is ulcerative colitis and the antibody is an ovine or equine polyclonal antibody (more preferably an ovine polyclonal antibody).

Inflammatory bowel disease is typically associated with symptoms such as frequent diarrhoea. Owing to reduced retention of a therapeutic in the intestine, high concentrations of antibody are required for treatment of inflammatory bowel disease. Monoclonal antibody therapy is therefore non-viable (e.g. due to high costs associated with production of monoclonal antibodies). Advantageously, a polyclonal antibody composition of the present invention provides a solution to the problem of treating inflammatory bowel diseases. Said polyclonal antibody composition is comparatively inexpensive to manufacture, thus providing a viable therapeutic.

A suitable therapeutic is required to exhibit high specificity for human TNFα. Advantageously, the blood-derived polyclonal antibodies (e.g. ovine or equine) (owing to the method of manufacture) demonstrate high specificity for human TNFα when compared to non-blood derived (and/or e.g. non-ovine or non-equine) antibodies and/or monoclonal antibodies. Furthermore, by definition, a composition comprising monoclonal antibodies will only bind to a single epitope whereas a composition comprising polyclonal antibodies will bind to several, thereby increasing the efficacy with which the human TNFα is neutralised.

The term "treat" or "treating" as used herein encompasses prophylactic treatment (e.g. to prevent onset of a disease) as well as corrective treatment (treatment of a subject already suffering from a disease). Preferably "treat" or "treating" as used herein means corrective treatment.

The term "treat" or "treating" as used herein refers to the disorder and/or a symptom thereof.

Therefore a composition of the invention may be administered to a subject in a therapeutically effective amount or a prophylactically effective amount.

A "therapeutically effective amount" is any amount of the antibody, which when administered alone or in combination to a subject for treating an inflammatory disorder (or a symptom thereof) is sufficient to effect such treatment of the disorder, or symptom thereof.

A "prophylactically effective amount" is any amount of the antibody that, when administered alone or in combination to a subject inhibits or delays the onset or reoccurrence of an inflammatory disorder (or a symptom thereof). In some embodiments, the prophylactically effective amount prevents the onset or reoccurrence of an inflammatory disorder entirely. "Inhibiting" the onset means either lessening the likelihood of an inflammatory disorder's onset (or symptom thereof), or preventing the onset entirely.

An appropriate dosage range is one that produces the desired therapeutic effect (e.g. wherein the antibody/composition is dosed in a therapeutically or prophylactically effective amount). A typical dosage regimen may comprise administering a composition of the invention once, twice, three times, four times, five times, six times or seven times per week. In one embodiment a dosage regimen comprises administering a composition of the invention daily, for example once or twice daily.

In one embodiment a composition of the invention is administered to a subject twice daily for the first four weeks of treatment. In some embodiments subsequent treatment is by way of once daily administration of the composition.

An appropriate dose may be 2 g or less (e.g. 1 g or less) of polyclonal antibodies. In one embodiment a dose is 0.5 g or less or 0.25 g or less of polyclonal antibodies.

In one embodiment intact polyclonal antibodies are administered at a dose of 2 g or less daily. In another embodiment the dose is 1 g or less daily, for example 0.5 g or 0.25 g or less daily.

Suitably, the doses above refer to the total amount of intact polyclonal antibodies comprised in a composition of the invention, suitably total intact polyclonal IgG (i.e. including antibodies that bind to TNFα and antibodies that do not bind to TNFα). The intact polyclonal antibodies may be obtainable directly from a blood sample (e.g. antisera) or a purified fraction thereof. Preferably, the intact polyclonal antibodies have been purified from a blood sample (e.g. an ovine blood sample), such as antisera. For example, the sample may have been subjected to precipitation (such as sodium sulphate precipitation), and filtration. Suitably, at least 5% (e.g. at least 10%) of the total intact polyclonal antibodies comprised in the composition bind to TNFα. More preferably at least 15% or at least 20% (such as at least 25% or at least 30%) of the total intact polyclonal antibodies comprised in the composition bind to TNFα.

It is surprising that a therapeutic/prophylactic effect is observed at such low doses of total intact blood-derived polyclonal antibody, and is demonstrative of the high concentration of specific antibody (i.e. that binds to TNFα) produced when compared to non-blood-derived source, such as milk. It is furthermore surprising that a therapeutic/prophylactic effect is observed at such low doses of total intact ovine or equine (preferably ovine) polyclonal antibody, and is demonstrative of the high concentration of specific antibody (i.e. that binds to TNFα) produced using an ovine or equine (preferably ovine) host.

In one embodiment, typical daily dosages are in the range of 5-20 mg (e.g. 8-15 mg or approximately 10 mg) of intact polyclonal antibodies per kg of body weight. The unit dosage can vary from less than 100 mg, but typically will be in the region of 250-500 mg per dose. Said dose may be administered daily (e.g. 1×, 2×, 3× or 4× per day).

In some embodiments an antibody composition of the invention may be administered to a subject in combination with one or more further therapeutic(s). Said one or more further therapeutic(s) may be administered sequentially or simultaneously with an antibody composition of the invention.

In one embodiment an antibody composition is administered in combination with a therapeutic that treats an inflammatory disorder (e.g. an inflammatory disorder referred to herein). Suitably, an antibody composition may be administered in combination with a therapeutic that treats an inflammatory bowel disorder (e.g. inflammatory bowel disease).

In one embodiment a therapeutic may be an aminosalicylate (5-ASA), a corticosteroid, an immunomodulator, an antibiotic or a biological therapy (e.g. a therapeutic antibody).

Examples of suitable therapeutics may include: prednisone, prednisolone sodium phosphate, budesonide, mesalamine, sulfasalazine, corticotropin, azathioprine, infliximab, hydrocortisone, methylprednisolone, methylprednisolone sodium succinate, mercaptopurine, dexamethasone, dexamethasone sodium phosphate, betamethasone acetate, betamethasone sodium phosphate, cyclosporine, cromolyn, mycophenolate mofetil, hydrocortisone sodium succinate, hydrocortisone acetate, triamcinolone acetonide, cortisone, methylprednisolone acetate, or combinations thereof, or pharmaceutically-acceptable salts thereof.

In one embodiment an antibody composition may be administered with one or more probiotic(s). The term "probiotic" as used herein means any live micro-organism(s) (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the gastrointestinal tract (e.g. the intestine).

The invention also provides a kit comprising an antibody composition of the invention, and instructions for use of same. The instructions may be for the use of the antibody composition in medicine, suitably for the use of the antibody composition in treating an inflammatory disorder. In one embodiment the instructions describe oral administration of the antibody composition to a subject. The instructions may alternatively or additionally describe an appropriate dosage regimen, for example any dosage regimen described herein.

In one embodiment the kit comprises a first container comprising the antibodies of the invention, a second container comprising means for protecting said antibodies during gastrointestinal transit, and instructions. Preferably the instructions describe a method for formulating the antibodies and means to obtain a composition of the invention.

In one embodiment a kit comprises one or more further therapeutic(s) described herein.

In another aspect the invention relates to a foodstuff comprising an antibody composition of the invention. The foodstuff may be any foodstuff in which the antibodies comprised in the antibody composition remain functional or in which a substantial concentration of said antibodies retain the ability to bind to and neutralise human TNFα. The term "substantial concentration" as used in this context means that at least 90%, for example at least 95% or 98% of the starting antibodies retain the ability to bind to and neutralise human TNFα.

The foodstuff may be a dairy product. In one embodiment a dairy product is selected from yogurt, cheese, or milk.

The foodstuff may comprise a probiotic, and optionally one or more prebiotic. The term "prebiotic" as used herein refers to a non-digestible food ingredient that beneficially affects the host by selectively stimulating the growth and/or the activity of one or more beneficial bacteria.

Sequence Comparison

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and "http://www.ncbi.nlm.nih.gov/" of the National Center for Biotechnology Information].

In one homology comparison, the identity exists over a region of the sequences that is at least 10 or 20 or 30 or 40 or 50 amino acid residues in length. In another homology comparison, the identity exists over a region of the sequences that is at least 60 or 70 or 80 or 90 or 100 amino acid residues in length.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{(Total number of identical matches)}}{\text{[length of the longer sequence plus the number of gaps introduced into the longer sequence in order to align the two sequences]}} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative amino acid substitutions may include:
Basic: arginine
 lysine
 histidine
Acidic: glutamic acid
 aspartic acid
Polar: glutamine
 asparagine
Hydrophobic: leucine
 isoleucine
 valine
Aromatic: phenylalanine
 tryptophan
 tyrosine
Small: glycine
 alanine
 serine
 threonine
 methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethyl homo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically aminoacylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively. The headings provided herein are not limitations of the various aspects or embodiments of this disclosure. Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. It is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure. It must be noted that as used herein and in the appended claims, the singular forms "a", "an", and "the" include plural referents unless the context clearly dictates otherwise. Thus, for example, reference to "an antibody" includes a plurality of such candidate agents and reference to "the antibody" includes reference to one or more antibodies and equivalents thereof known to those skilled in the art, and so forth. The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

FIGURES

Embodiments of the invention will now be described, by way of example only, with reference to the accompanying Figures, in which.

Figure 3:
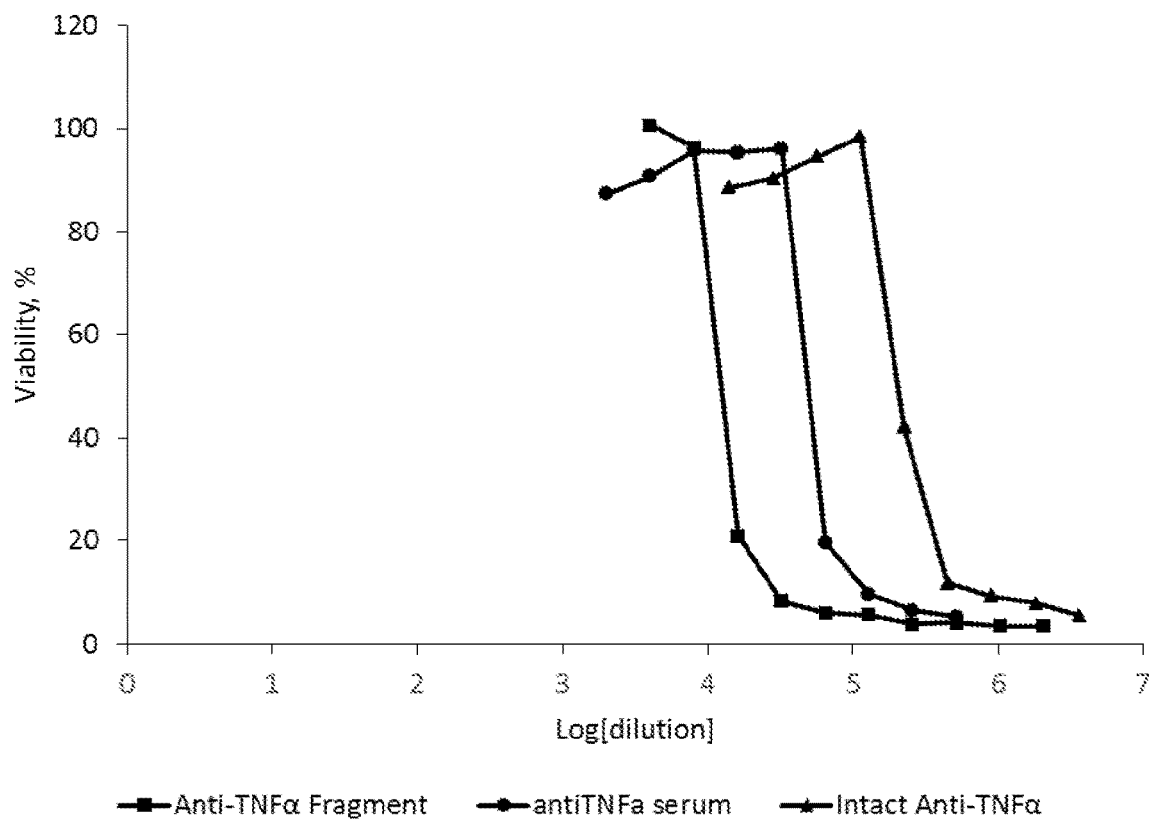

FIG. 3 shows results of an immunocytotoxicity assay (IOTA) testing the neutralising activity of Anti-TNFα Fragment (■), Intact Anti-TNFα (▲) and TNFα antisera (●) using L929 cells. Starting concentration: Anti-TNFα Fragment –50 mg/ml; Intact Anti-TNFα –210 mg/ml; TNFα antisera protein concentration –86 mg/ml.

Figure 4:
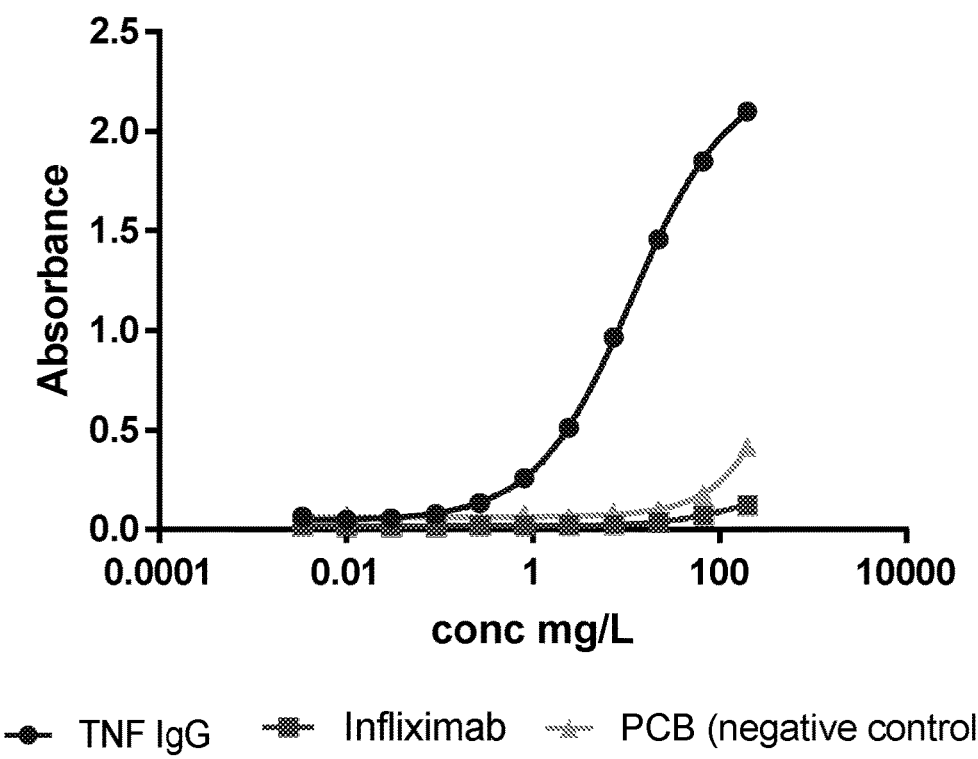

FIG. 4 shows the results of an ELISA comparing binding to murine TNFα by ovine blood-derived intact PcAbs (anti-human TNFα IgG) and monoclonal antibody Infliximab. Anti-human TNFα IgG (●), Infliximab (■), and negative control (PCB) (▲).

EXAMPLES

Example 1

Preparation of Ovine Antisera to Human TNFα

Mature human TNFα (hTNFα) (UniProtKB Accession No.: P01375) was obtained from R&D Systems, Boehringer. The amino acid sequence is shown as SEQ ID No. 1.

The immunogen for the primary immunisation of merino wether sheep comprised Freund's complete adjuvant and 100 μg of hTNFα per sheep. The protein:adjuvant mixture was injected subcutaneously and equally into 6 injection sites chosen for their proximity to the axillary, inguinal, and prescapular drainage lymph glands. Each sheep was reimmunized at 28-day intervals with 100 μg of hTNFα and Freund's incomplete adjuvant, and blood samples were collected 14 days later at approximately 4 weekly intervals at processing facilities at Turretfield Research Centre (Rosedale, South Australia, Australia) according to strict state and national ethical guidelines for animal welfare. The animals were not terminally bled. A total of 10 mL of blood per kg of body weight can be collected from the external jugular vein without detriment to the animal.

Ovine antisera was subsequently stored at −20° C.

Example 2

Purification of Polyclonal Ovine Antibodies to Human TNFα (Intact Anti-TNFα)

Two different methods for purification of ovine PcAb were used in order to determine which method would co-isolate to a larger extent the efficient inhibitor of human trypsin, α1-anti-trypsin. Either caprylic acid precipitation, which precipitates albumin and keeps the IgG in solution, or the sodium sulphate precipitation that precipitates IgG were used. The purified IgG was filtered and stored at −20° C. ready for inclusion in the proposed formulation for oral administration or for further characterisation.

The presence of protease inhibitors in antisera and the two IgG fractions purified using either caprylic acid or sodium sulphate was assayed against trypsin and chymotrypsin by way of a colorimetric assay. The assay was based on the methods of Kakade M L et al. Determination of trypsin inhibitor activity of soy products: a collaborative analysis of an improved procedure. Cereal Chem 51: 376-381, 1974 (which is incorporated herein by reference) and measured cleavage of Na-Benzoyl-DL-Arginine-p-Nitroanilide Solution (L-BAPNA) (colourless) to p-nitroanaline (a yellow substrate) by trypsin.

Figure 1:
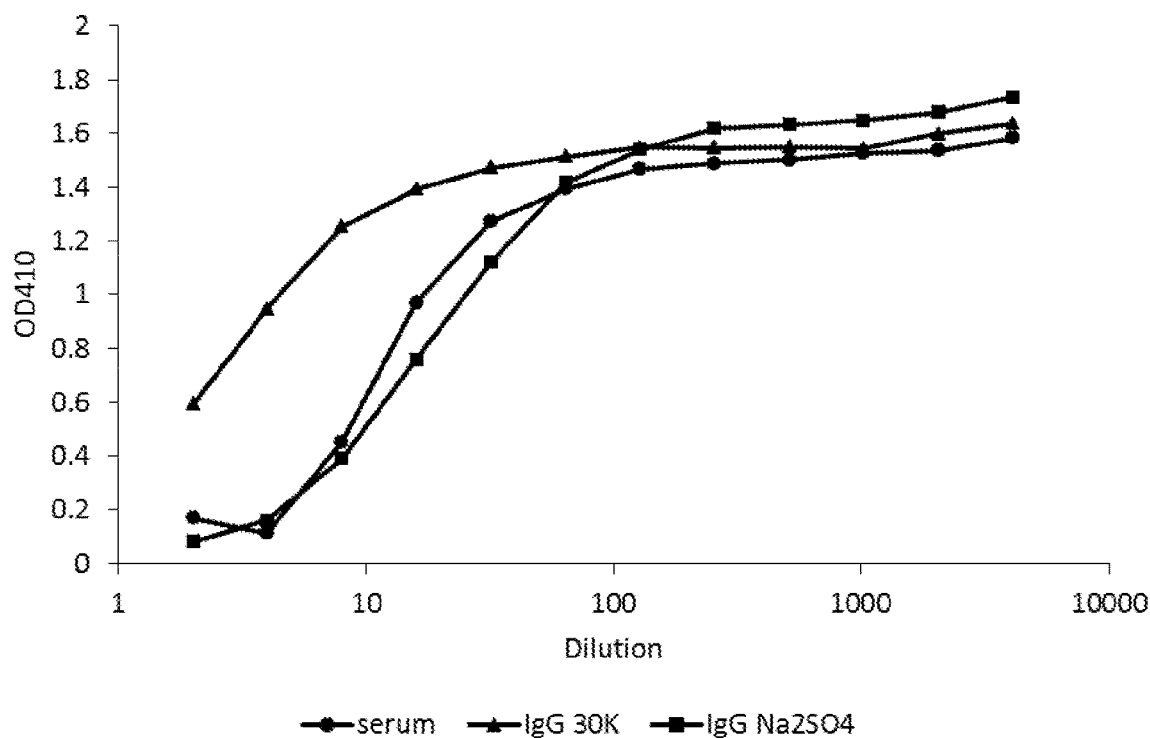
FIG. 1 shows inhibition of bovine trypsin by Intact Anti-TNFα purified with either caprylic acid (▲) or sodium sulphate (■). TNFα antisera (●) was used as a control.

Two-fold dilutions of inhibitor sample were diluted in 50 mM Tris-buffer, pH 8.2, containing 20 mM $CaCl_2$ (100 μl final volume) across a 96-well plate (Grenier UV-Star). To each well, 100 μl of trypsin (0.2 mg/ml diluted in 1 mM HCL) or chymotrypsin (1 mg/ml in WFI) solution was added followed by 100 μl of either L-BAPNA or NSLPN (2 mM in DMSO) for trypsin or chymotrypsin, respectively. Reactions were terminated after 5 minutes for the trypsin assay and after 60 minutes for the chymotrypsin assay with the addition of 50 μl stop solution (30% v/v acetic acid) and the absorbance measured spectrophotometrically at 410 nm using Omega PolarStar. Blank samples were prepared by adding the stop solution prior to the substrate solution. The average absorbance value was then plotted against the dilution, resulting in a dose response curve. Representative curves are shown in FIG. 1, which demonstrate that the sodium sulphate purification retains the α1-anti-trypsin inhibitor much better that the caprylic acid precipitation procedure.

These two methods can also be used to assess the survival of protease inhibitors in the oral formulation after incubation in simulated gastric and intestinal fluids.

Example 3

Enzyme-Linked Immunosorbent Assay for Characterising Antibody Binding

The specific antibodies produced bound to multiple epitopes on the surface of recombinant human TNFα (rhTNFα) but not to recombinant rodent TNFα. The avidity of binding was extremely high.

A direct ELISA assay was developed for detection of anti-TNFα IgG in the ovine antisera and in the purified fraction of IgG (purified by way of caprylic acid precipitation) from this antisera (Intact Anti-TNFα). Immulon 4HBx microtiter plates were coated with 1 μg/mL hTNFα. Plates were washed with 3 changes of phosphate-buffered saline (PBS) containing 0.1% Tween 20 (PBST) and blocked for 1 hour at 37° C. with blocking buffer (2.5% fetal calf serum diluted in PBS). Plates were washed and incubated for 1 hour at 37° C. with antisera at initial dilutions of 1:1000, followed by 1:2 serial dilutions; washed with PBST; and incubated with a donkey anti-ovine IgG horseradish peroxidase conjugate for 1 hour at 37° C. After further washing, 3,3',5,5'-Tetramethylbenzidine (TMB) liquid substrate solution was added, and the reaction was stopped after approximately 10 minutes by the addition of 1.0 M HCL before reading the optical density at 450 nm.

Figure 2:
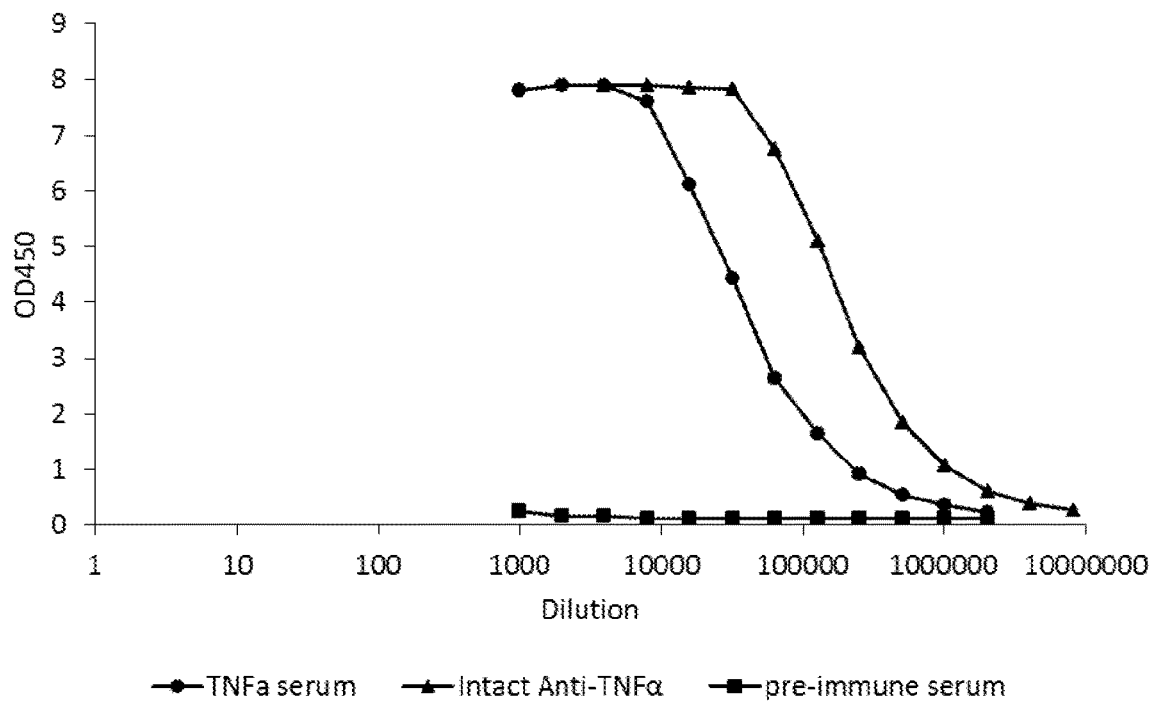
FIG. 2 shows results of a direct ELISA for detection of anti-TNFα IgG in antisera (●) and IgG purified by way of caprylic acid precipitation (▲).

The developed assay showed very low background which was tested using pre-immune ovine serum (FIG. 2).

Example 4

Immunocytotoxicity Assay for Characterising Antibody Neutralisation

The L929 mouse fibrosarcoma cell line (commercially available from Sigma-Aldrich, The Old Brickyard, New Road, Gillingham, Dorset, SP8 4XT, UK) was used to test the cytotoxic effects of TNFα as well as the neutralising ability of antibodies to TNFα. An assay was therefore developed to test neutralisation of the cytotoxic effect of rhTNFα by the ovine PcAb in the antisera, and by purified IgG from the antisera (Intact Anti-TNFα), and by fragments thereof (Anti-TNFα Fragment).

Anti-TNFα Fragment was prepared by subjecting a portion of the stock of ovine antisera of Example 1 to papain digestion. The Fab were present at a concentration of 10 g/L and about 10% of the total Fab were specific for TNFα. An affinity chromatography step was not included in its manufacture. In the presence of excess of Fab, about 12 molecules of Fab become attached to each TNFα trimer.

As a challenging dose we used the 1090 hTNFα concentration of 13 ng/ml determined from a cytotoxicity assay (data not shown). Briefly, L929 cells containing twice the necessary challenging dose in DMEM were co-incubated with an equal volume of various dilutions of hTNFα antisera or Anti-TNFα Fragment or Intact Anti-TNFα for 24 h. As a positive control (maximum killing), 2.5 μg/ml hTNFα was used. Antibody toxin neutralisation titres were estimated by colorimetric assays based on cell staining with neutral red.

Antibody toxin neutralisation titres were estimated by colorimetric assays based on cell staining with neutral red (representative curves shown in FIG. 3).

The specific antibody concentration was calculated as follow:

$$\text{Specific } Ab \text{ conc } [g/L] = [CCD(\mu g/L) - LC50(\mu g/L)] \times [MW\, Ab/(MW\, Ag \times BS)] \times EC50 \times 10^{-6}$$

CCD (µg/L)–challenging dose=13 µg/L (LC90 determined from the TNFα cytotoxicity on L929 cells)
LC50 (µg/L)=0.3 µg/L (determined from the TNFα cytotoxicity on L929 cells)
BS–binding sites=2 for whole IgG
MW Ab=160 000 Da
MW Ag (TNFα)=51 000 Da Taking the above into account, the specific PcAb concentration in the antisera was calculated at 2.9 g/L.

Example 5

Formulation of Intact Anti-TNFα

The choice of protease inhibitors to protect the PcAb of the invention (Intact Anti-TNFα) from digestion as well as the inhibitor's survival in gastric and intestinal fluids was assessed against trypsin and chymotrypsin using colourimetric assay, based on the method of Kakade M L et al. Determination of trypsin inhibitor activity of soy products: a collaborative analysis of an improved procedure. Cereal Chem 51: 376-381, 1974. The trypsin assay is described above. The chymotrypsin assay utilised a colourless NSLPN substrate producing a yellow colour.

The two antacids in Table 1, magnesium hydroxide and aluminium hydroxide gel, were added to neutralise the low gastric pH, and thereby prevent pepsin in the stomach from degrading the active components of Intact Anti-TNFα—the ovine IgG against TNFα and the egg white trypsin and chymotrypsin inhibitors. Other constituents were antimicrobials methylparaben and propylparaben which are believed to maintain a low bioburden. The antifoaming agent simethicone was added to prevent protein denaturation when the suspension is mixed prior to use. Sweeteners in the form of sodium saccharin and mannitol reduce the bitterness of the two antacids. A flavouring agent, peppermint oil, was used to improve the taste. A suspending agent, xanthan gum, was added to keep all the above components in suspension.

It was experimentally determined that adding 200 mM Glycine to the formulation significantly improved stability of the suspension.

TABLE 1

Composition of Intact Anti-TNFα oral formulation.

| Category | | Material name | Concentration |
| --- | --- | --- | --- |
| Active components | IgG | Intact Anti-TNFα | 50 g/l |
| Excipients | Protease inhibitor | Egg white dried (EWD) | 60 g/l |
| | Antacid | Magnesium hydroxide | 23.4 g/l |
| | | Dried aluminium hydroxide gel | 26.4 g/l |
| | Antimicrobial | Methylparaben (E218) | 2 g/l |
| | | Propylparaben (E216) | 0.6 g/l |
| | Suspension stability | Glycine (200 mM) | 15 g/l |
| | Antifoaming agent | Simethicone | 16.89 g/l |
| | Sweeteners | Sodium saccharin | 0.4 g/l |
| | | Mannitol | 21 g/l |
| | Flavour | Peppermint oil | 0.2 g/l |
| | Suspending agent | Xanthan gum | 4 g/l |

Example 6

Physicochemical Characterisation of the Composition Formulated for Oral Delivery The physical appearance of the suspension and its purity were ensured by carefully performing visual inspections. Sedimentation volume of the suspension was determined by pouring 50 ml of the formulation into a 100 ml measuring cylinder and the sedimentation volume was monitored and recorded at different time intervals.

Duplicate results were obtained and the sedimentation volume was calculated according to the equation:

$$F = Vu/Vo$$

Where F is sedimentation volume, Vu—ultimate height of sediment and Vo—initial height of total suspension.

Within 48 hours of the beginning of the sedimentation experiment, no sedimentation was observed (Vu=0). Therefore, the pharmaceutical suspension remained very stable within 48 hours without any separation. Furthermore, after 48 hours the cylinder with the suspension was turned upside-down and none of the layers were observed to be disposed at the bottom of the cylinder. This demonstrates that there were no layers forming within the suspension. In other word, there was no flocculation observed within the prepared suspension during the 48-hour period of the experiment.

Example 7

Case Study

A 27 year old white male on an emergency admission to hospital is diagnosed as suffering from acute, severe ulcerative colitis which is confirmed by colonoscopy and biopsy. The subject is immediately administered an intravenous course of hydrocortisone but fails to respond over the next six days. There is concern that he might require a total colectomy and, consequently, he is orally administered a formulation of the invention (e.g. as per Example 5). For the first two weeks he receives 50 ml twice daily and, thereafter, 50 ml daily for a further 12 weeks.

The patient makes a quick and excellent recovery based on his answers to the UK bowel disease questionnaire (UK-IBDQ) and various clinical parameters. In addition measured parameters such as C-reactive protein return to normal values, and he experiences no serious adverse effects. At the end of the study there is significant mucosal healing as assessed by a second colonoscopy and biopsy.

Example 8

Synergistic Effects of the Compositions Formulated for Oral Delivery

The following formulations are provided:
Formulation A: Intact Anti-TNFα;
Formulation B: Egg White Dried Protease Inhibitor;
Formulation C: Bowman-Birk Inhibitor (soybean);

Formulation D: Intact Anti-TNFα+Egg White Dried Protease Inhibitor; and

Formulation E: Intact Anti-TNFα+Bowman-Birk Inhibitor (soybean).

25 patients with ulcerative colitis and 25 patients with Crohn's Disease provide consent to be involved in a study to test the efficacy of Formulations A-E. The patients are split into groups of 5 and administered one of Formulations A-E (i.e. 5 patients with ulcerative colitis are administered Formulation A and 5 patients with Crohn's Disease are administered Formulation A, 5 patients with ulcerative colitis are administered Formulation B and 5 patients with Crohn's Disease are administered Formulation B, etc.). The dosage regime is 20 ml (equivalent to 1 g of Intact Anti-TNFα) twice daily for 4 weeks, and once daily thereafter.

Physicians determine that patients in both disease groups administered Formulations D and E show a greater improvement and reduced symptoms when compared with patients administered Formulations A-C. Colonoscopies reveal an improvement in the surface layers of the intestinal tract post-treatment. The improvement in patients administered Formulations D and E is much greater than the improvement in patients administered Formulations A-C, and much greater than the expected combined improvement of Formulations A+B and Formulations A+C (as determined by way of colonoscopy). Thus, the combination of PcAbs and protease inhibitors (e.g. EWD protease inhibitors and/or Bowman-Birk Inhibitors) yields unexpected synergistic effects.

Comparative Example 9

Comparative Analysis of Specific Antibody Titres from Sheep Serum (Ovine) & Hen Eggs A study was undertaken to assess the concentration and avidities of specific IgY obtained from hen eggs in comparison with specific antibody concentrations from ovine antisera.

A group of 10 chickens and 5 sheep were immunised with human interleukin-6 (hIL-6, a pro-inflammatory cytokine like TNFα) and the titres and avidities of the resultant specific PcAb was compared. The average avidity constants were $1.3 \times 10^{10}$ L/mol for chicken IgY vs $3.1 \times 10^{10}$ L/mol for the ovine antibodies. However, the levels of specific PcAb attained in the sheep (with an average titre of ≥1:200,000) were more than ten times the titres found in egg yolk (≤1:20,000). This tenfold or more difference in the concentration of specific PcAb was also apparent when sheep and hens were immunised with a number of other immunogens.

The above experiment shows the advantages of antibodies derived from blood, and from an ovine source in particular.

Example 10

Comparative Analysis of Specific Antibody Titres Sourced from Sheep Serum (Ovine) & Cow's Milk (Bovine)

A study was undertaken to assess the potential of colostrum and milk from suitably immunised cows as a source of PcAb.

Cows were immunised with human TNFα and the titres of the resulting specific PcAb determined first in the colostrum and then in serial samples of milk. The maximum titre obtained in colostrum was 1:275,000 (as compared with 1:800,000 in ovine antisera) and, after the first milking, levels rapidly fell to approximately 1:27,500.

Thus, blood-derived sources were shown to yield higher concentrations of antibodies that bind to human TNFα when compared to milk/colostrum-derived sources.

Example 11

Stability of Oral Antibody Formulations

The oral formulation of Example 5 was tested for antibody binding and neutralising activity following storage for approximately 12 months. It was shown that there was no deterioration in protease inhibitor activity, and no change in the physical stability of the formulation, which retained antibody binding and neutralising activity.

Example 12

Efficacy of Antimicrobials of the Oral Antibody Formulations

The antimicrobial agents in the oral formulation of Example 5—Methylparaben (E218) (concentration 2 g/L) and Propylparaben (E216) (0.6 g/L)—were subjected to external antimicrobial testing to European Pharmacopeia standards for such organisms as *S. aureus, P. aeruginosa, E. coli, C. albicans* and *A. brasiliensis*. Complete sterility was shown.

Example 13

Comparison of Blood-Derived Polyclonal Antibodies with Monoclonal Antibodies

A comparative antigen-binding assay was performed using blood-derived (ovine) polyclonal antibodies that bind to human TNFα and Infliximab (Schering-Plough Ltd), a monoclonal antibody that binds to human TNFα.

FIG. 4 shows that the monoclonal antibody, Infliximab, does not bind to murine TNFα, whereas the ovine derived polyclonal antibodies raised towards human TNFα do.

The blood-derived polyclonal antibodies of the invention were shown to bind to and neutralise murine TNFα albeit at a concentration approximately 100-fold higher than that needed to neutralise human TNFα. No neutralisation of murine TNFα was observed by Infliximab, indicative of an overall reduced neutralisation capability when compared to antibodies of the invention.

SEQUENCES

SEQ ID No. 1
VRSSSRTPSDKPVAHVVANPQAEGQLQWLNRRANALLANGVELRDNQ
LVVPSEGLYLIYSQVLFKGQGCPSTHVLLTHTISRIAVSYQTKVNLL
SAIKSPCQRETPEGAEAKPWYEPIYLGGVFQLEKGDRLSAEINRPDY
LDFAESGQVYFGIIAL

SEQ ID No. 2
MSTESMIRDVELAEEALPKKTGGPQGSRRCLFLSLFSFLIVAGATTL
FCLLHFGVIGPQREEFPRDLSLISPLAQAVRSSSRTPSDKPVAHVVA
NPQAEGQLQWLNRRANALLANGVELRDNQLVVPSEGLYLIYSQVLFK
GQGCPSTHVLLTHTISRIAVSYQTKVNLLSAIKSPCQRETPEGAEAK
PWYEPIYLGGVFQLEKGDRLSAEINRPDYLDFAESGQVYFGIIAL

SEQ ID No. 3
MSTESMIRDVELAEEALPKKTGGPQGSRRCLFLSLFSFLIVAGATTL
FCLLHFGVIGPQREEFPRDLSLISPLAQAVRSSSRTPSDKPVAHVVA
NPQAEGQLQWLNRRANALLANGVELRDNQLVVPSEGLYLIYSQVLFK
GQGCP

SEQ ID No. 4
VRSSSRTPSDKPVAHVVANPQAEGQLQWLNRRANALLANGVELRDNQ
LVVPSEGLYLIYSQVLFKGQGCP

SEQUENCES

SEQ ID No. 5
VRSSSRTP

SEQ ID No. 6
HVVANPQAEGQLQWLNRR

SEQ ID No. 7
NGVELR

SEQ ID No. 8
VPSEG

SEQ ID No. 9
CPSTHVL

SEQ ID No. 10
ISRIAVSYQTK

SEQ ID No. 11
PCQRETPEGAEAK

SEQ ID No. 12
DRLSAEINRPDYLDFA

SEQUENCES

SEQ ID No. 13 (Variant Human TNFα P84L)
MSTESMIRDVELAEEALPKKTGGPQGSRRCLFLSLFSFLIVAGATTL
FCLLHFGVIGPQREEFPRDLSLISPLAQAVRSSSRTLSDKPVAHVVA
NPQAEGQLQWLNRRANALLANGVELRDNQLVVPSEGLYLIYSQVLFK
GQGCPSTHVLLTHTISRIAVSYQTKVNLLSAIKSPCQRETPEGAEAK
PWYEPIYLGGVFQLEKGDRLSAEINRPDYLDFAESGQVYFGI IAL All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An antibody composition for oral administration comprising:
   a. intact blood-derived polyclonal antibodies that bind to a human tumour necrosis factor a (TNFα); and
   b. a protease inhibitor and/or an antacid,
wherein the intact blood-derived polyclonal antibodies are derived from serum or plasma of an ovine mammal administered TNFα or a fragment thereof.

2. The antibody composition of claim 1, wherein the antibody composition and the intact blood-derived polyclonal antibodies therein have not been affinity purified.

3. The antibody composition of claim 1, wherein the intact blood-derived polyclonal antibodies are purified using sodium sulphate precipitation or caprylic acid precipitation, and optionally, filtration.

4. The antibody composition of claim 1, wherein the protease inhibitor is selected from the Bowman-Birk inhibitor family of proteins.

5. The antibody composition of claim 1, wherein the protease inhibitor comprises one or more of:
   a. a polypeptide which binds specifically to and suppresses or inactivates the proteolytic activity of trypsin and/or chymotrypsin; and/or b. an antibody that binds to trypsin and/or chymotrypsin and suppresses or inactivates the protease activity of said trypsin and/or chymotrypsin.

6. The antibody composition of claim 1, wherein the protease inhibitor comprises egg whites.

7. The antibody composition of claim 6, wherein the egg whites comprise powdered egg whites.

8. The antibody composition of claim 1, wherein the protease inhibitor comprises ovomucoid, ovostatin, ovomacroglobulin, or combinations thereof.

9. The antibody composition of claim 1, formulated as a liquid.

10. The antibody composition of claim 1, wherein at least 5% of the total antibodies present in the composition bind to TNFα.

11. The antibody composition of claim 1, wherein at least 10% of the total antibodies present in the composition bind to TNFα.

12. A method for manufacturing an antibody composition for oral administration, said method comprising:
   a. obtaining a blood sample from an ovine mammal that has been administered an immunogen comprising human tumour necrosis factor a (TNFα) or a fragment thereof, thereby providing a sample comprising intact blood-derived polyclonal antibodies that bind to TNFα;
   b. admixing the intact blood-derived polyclonal antibodies that bind to human TNFα with a protease inhibitor and/or an antacid.

13. The method of claim 12, wherein the obtaining further comprises obtaining serum from the blood sample.

* * * * *